US012596121B2

(12) United States Patent
Hegge et al.

(10) Patent No.: US 12,596,121 B2
(45) Date of Patent: Apr. 7, 2026

(54) COMPANION DIAGNOSTIC METHOD FOR USE IN THE TREATMENT OF IRRITABLE BOWEL SYNDROME WITH DIETARY INTERVENTIONS OR FAECAL MICROBIOTA TRANSPLANT

(71) Applicant: Genetic Analysis AS, Okern (NO)

(72) Inventors: Finn Terje Hegge, Oslo (NO); Christina Casen, Oslo (NO); Jorgen Valeur, Oslo (NO); Arne Roseth, Oslo (NO); Milada Cvancarova Smastuen, Oslo (NO)

(73) Assignee: Genetic Analysis AS, Oslo (NO)

( * ) Notice: Subject to any disclaimer, the term of this patent is extended or adjusted under 35 U.S.C. 154(b) by 1074 days.

(21) Appl. No.: 17/562,416

(22) Filed: Dec. 27, 2021

(65) Prior Publication Data

US 2022/0120747 A1      Apr. 21, 2022

Related U.S. Application Data

(62) Division of application No. 17/007,277, filed on Aug. 31, 2020, now Pat. No. 11,243,203, which is a division of application No. 16/341,309, filed as application No. PCT/EP2017/076261 on Oct. 13, 2017, now Pat. No. 10,794,909.

(30) Foreign Application Priority Data

Oct. 14, 2016    (GB) ...................................... 1617519

(51) Int. Cl.
    *G01N 33/569*          (2006.01)

(52) U.S. Cl.
    CPC . *G01N 33/56916* (2013.01); *G01N 2800/065* (2013.01); *G01N 2800/52* (2013.01)

(58) Field of Classification Search
    None
    See application file for complete search history.

(56) References Cited

U.S. PATENT DOCUMENTS

| | | | | |
|---|---|---|---|---|
| 2012/0238468 A1* | 9/2012 | Tuk | ........................ | C12Q 1/689 |
| | | | | 506/9 |
| 2020/0049708 A1 | 2/2020 | Hegge et al. | | |
| 2020/0400666 A1 | 12/2020 | Hegge | | |

FOREIGN PATENT DOCUMENTS

| | | |
|---|---|---|
| CN | 105543385 A | 5/2016 |
| WO | 199851693 A1 | 11/1998 |
| WO | 200153525 A2 | 7/2001 |
| WO | 2007050656 A2 | 5/2007 |
| WO | 2011043654 A1 | 4/2011 |
| WO | 2012080754 A2 | 6/2012 |
| WO | 2013171515 A1 | 11/2013 |
| WO | 2015171493 A1 | 11/2015 |
| WO | 2016066175 A1 | 5/2016 |
| WO | 2016156251 A1 | 10/2016 |

OTHER PUBLICATIONS

Bennet et al.; "Multivariate Modelling of Faecal Bacterial Profiles of Patients with IBS Predicts Responsiveness to a Diet Low in FODMAPs and Supplement"; Gut; 13, pp. 872-881; doi: 10.1136/gutjnl-2016-313128; (2017).
Betz et al.; Validation of the IBS SSS; Z Gastroenterol; 51(10); pp. 1171-1176; (2013).
Casen et al.; "Deviations in Human Gut Microbiota: A Novel Diagnostic Test for Determining Dysbiosis in Patients With IBS or IBD"; Alimentary Pharmacology and Therapeutics; 42; 2015; pp. 71-83.
Chumpitazi et al.; "Gut Microbiota Influences Low Fermentable Substrate Diet Efficacy in Children With Irritable Bowel Syndrome"; Gut Microbes 5:2; pp. 165-175; (2014).
Chumpitazi et al.; "Randomised Clinical Trial: Gut Microbiome Biomarkers are Associated with Clinical Response to a Low FODMAP Diet in Children with Irritable Bowel Syndrome"; Aliment Pharmacol Ther. 42(4); pp. 418-427; (2015).
Francis et al.; "The Irritable Bowel Severity Scoring System: A Simple Method of Monitoring Irritable Bowel Syndrome and its Progress"; Aliment Pharmacol Ther; 11; pp. 395-402; (1997).
GB1617519.2 Search Report Under Section 17(5); date of search Jul. 26, 2017; 5 pages.
Gearry et al.; "Reduction of Dietary Poorly Absorbed Short-chain Carbohydrates (FODMAPs) Improves Abdominal Symptoms in Patients with Inflammatory Bowel Disease—a Pilot Study"; Journal of Crohn's and Colitis; 3; pp. 8-14; (2009).
International Search Report and Written Opinion; International Application No. PCT/EP2017/076261; International Filing Date Oct. 13, 2017; Date of Mailing Dec. 6, 2017; 15 pages.
Kelly et al.; "Update on FMT 2015: Indications, Methodologies, Mechanisms and Outlook"; Gastroenterology; 149(1); pp. 223-237; (2015).
Magnusson et al.; "Anti-TNF Therapy Response in Patients with Ulcerative Colitis Is Associated with Colonic Antimicrobial Peptide Expression and Microbiota Composition"; Journal of Crohn's and Colitis; 10; pp. 943-952; doi: 10.1093/ecco-jcc/jw051; (2016).

(Continued)

*Primary Examiner* — Brian Gangle
(74) *Attorney, Agent, or Firm* — Karen LeCuyer; DeWitt LLP

(57) ABSTRACT

The present invention provides a diagnostic method which may be used to determine the likelihood that a subject with Irritable Bowel Syndrome (IBS) will respond to treatment with an IBS intervention diet. In particular, the method may be used to predict, or determine the likelihood of, a positive response of the subject with IBS to treatment with an IBS intervention diet, especially to determine the likelihood that the dietary intervention may have a positive (i.e. beneficial) effect on the subject's GI tract, specifically the GI tract microbiota, or other symptoms or complications of IBS (e.g. reducing severity thereof). The method of the present invention is based on analysing the abundance of certain bacteria in GI tract samples, e.g. by nucleic acid analysis.

9 Claims, 11 Drawing Sheets

(56) References Cited

OTHER PUBLICATIONS

Slavin, Joanne; "Fiber and Prebiotics: Mechanisms and Health Benefits"; Nutrients; 5; pp. 1417-1435; (2013).

Smits et al.; Individualized Responses of Gut Microbiota to Dietary Intervention Modeled in Humanized Mice; mSystems; vol. 1(5); 2016; e00098-16; 6 pages.

UEG Week; Press Release; Embargoed: 00:00 CET, Tuesday, Oct. 18, 2016; "New Breakthrough for IBS Patients"; 3 pages; www.ueg.eu.

Vebo et al.; "Temporal Development of the Infant Gut Microbiota in Immunoglobulin E-Sensitized and Nonsensitized Children Determined by the GA-Map Infant Array"; Clinical and Vaccine Immunology; 2011; (18);pp. 1326-1335.

* cited by examiner

COMPANION DIAGNOSTIC METHOD FOR USE IN THE TREATMENT OF IRRITABLE BOWEL SYNDROME WITH DIETARY INTERVENTIONS OR FAECAL MICROBIOTA TRANSPLANT

CROSS REFERENCE TO RELATED APPLICATIONS

This application is a Divisional of U.S. application Ser. No. 17/007,277, filed Aug. 31, 2020, which is is a Divisional of U.S. application Ser. No. 16/341,309 filed on Apr. 11, 2019, which is a National Stage application of PCT/EP2017/076261, filed Oct. 13, 2017, which claims the benefit of GB Application No. 1617519.2, filed on Oct. 14, 2016, which are incorporated by reference in their entirety herein.

BACKGROUND

The present invention provides a diagnostic method which may be used to determine the likelihood that a subject with Irritable Bowel Syndrome (IBS) will respond to treatment with an IBS intervention diet or faecal microbiota transplant (FMT). In particular, the method may be used to predict, or determine the likelihood of, a positive response of the subject with IBS to treatment with an IBS intervention diet or FMT, especially to determine the likelihood that the dietary intervention or FMT may have a positive (i.e. beneficial) effect on the subject's GI tract, specifically the GI tract microbiota, or other symptoms or complications of IBS (e.g. reducing severity thereof). In this way, it may be determined whether or not IBS, or a complication or symptom of IBS, in a subject with IBS will improve, or the development of IBS, or said complication or symptom of IBS, in said subject will be prevented or delayed, following treatment with an IBS intervention diet or FMT. The method of the invention thereby permits the identification of IBS patients who are likely to respond clinically to treatment with an IBS intervention diet or FMT.

Surprisingly, it has been found that, in IBS subjects which are shown to respond to treatment with an IBS intervention diet or FMT, the abundance of bacteria from certain taxonomic groups in faecal samples may be either greater or less than that in subjects non-symptomatic for IBS or IBS subjects which are shown to not respond to treatment with an IBS intervention diet or FMT. Thus by comparing the amounts of these bacteria in GI tract samples from subjects with IBS with the amounts in corresponding samples from subjects non-symptomatic for IBS, IBS subjects which are likely to respond to treatment with an IBS intervention diet or FMT may be identified. It follows that alternatively, or additionally, the amounts of these bacteria in GI tract samples from subjects with IBS may be compared with median values for the amounts of these bacteria from GI tract samples from subjects previously shown to be responsive to said treatments and test values greater than a median cut-off value for bacteria from taxonomic groups for which responders show increased amounts compared to non-responders, or test values which are less than a median cut-off value for bacteria from taxonomic groups for which responders show decreased amounts compared to non-responders, are indicative of IBS subjects which are likely to respond to treatment with an IBS intervention diet or FMT. The method of the present invention is therefore based on analysing the abundance of certain bacteria in GI tract samples, e.g. by nucleic acid analysis including nucleic acid sequence techniques or oligonucleotide probe hybridisation-based techniques.

IBS is a functional gastrointestinal disorder defined by reference to the presence of a combination of symptoms, specifically chronic abdominal pain or discomfort and prolonged periods of diarrhoea, constipation or alternating periods of both (IBS-Diarrhoea (diarrhoea subtype IBS), IBS-Constipation (constipation subtype IBS) and IBS-Mixed (mixed subtype IBS). A commonly accepted diagnostic standard is the Rome III criteria, i.e. recurrent abdominal pain or discomfort ("discomfort" meaning an uncomfortable sensation not described as pain) at least 3 days per month in the last 3 months associated with two or more of the following: improvement with defecation, onset associated with a change in frequency of stool, onset associated with a change in form (appearance) of stool. Some patients also experience bloating, abdominal distension, spasm, flatulence, tenesmus and bowel urgency. Unlike Inflammatory Bowel Disease (IBD), IBS is an idiopathic condition that is not believed to be triggered by an underlying pathological mechanism, but often the same symptoms are seen. IBS can be diagnosed from the detection of the characteristic symptoms, but typically more invasive tests such as blood tests and endoscopic investigations may be required to rule out alternative causes of the symptoms displayed. IBS severity may be measured with the now established IBS Symptom Severity Score (IBS-SSS; Francis C. Y., Aliment Pharmacol Ther. 1997 April; 11(2):395-402) which has been found to be a valid, meaningful and reproducible questionnaire with a high sensitivity to assess changes in symptom severity, especially in IBS patients with moderate symptoms (Betz, C., et al, Z Gastroenterol., 2013, 51(10):1171-6).

Clinically effective treatments for IBS are limited in number but include administration of antibiotics (e.g. rifaximin), dietary interventions including diets rich in prebiotics (e.g. high fermentable oligosaccharides (FOS) diets (Slavin J. Nutrients. 2013 April; 5(4): 1417-1435)), diets restricted in prebiotics (e.g. restricted FODMAP (Fermentable Oligosaccharides, Disaccharides, Monosaccharides and Polyols) diets (Gearry R. B et al, JCC 2008.09.004 8-14)), and diets rich in probiotics, and transplants of faecal microbiota (FMT; Kelly C R et al. Gastroenterology. 2015 July; 149(1): 223-237). Other specific treatments include linaclotide, in particular for symptomatic treatment of moderate to severe irritable-bowel syndrome with constipation (IBS-C) in adults; and eluxadoline, in particular in the treatment of diarrhoea and abdominal pain in individuals with diarrhoea-predominant irritable bowel syndrome (IBS-D). Moreover, given the idiopathic nature of IBS, it is often seen that a treatment which is effective in one patient is not effective in another, even if each patient displays essentially the same outward symptoms. Even a single patient may be responsive at certain times but not others.

The GI tract, also referred to as the digestive tract or alimentary canal (and which terms may be used interchangeably with GI tract), is the continuous series of organs beginning at the mouth and ending at the anus. Throughout its length the GI tract is colonised by microorganisms of a variety of different species. Together the microorganism content of the GI tract is the microbiota of the GI tract. The relative amounts of the constituent microorganisms or groups thereof can be considered to be a profile of the microbiota. Microbiota profiles therefore give information on microbial diversity (i.e. the number of taxonomically distinct microbes or distinct taxonomic groups which are present) in the GI tract as well as providing information on the relative amounts of the microbes or groups thereof which are present.

Many diseases and conditions, or stages thereof, are believed to be associated with perturbations in the microbiota of the GI tract, or regions thereof. In some instances the disease or condition may be caused by, or is exacerbated by, the shift in the profile of the microbiota of the GI tract, or regions thereof (i.e. the relative amounts of constituent microbes and the diversity of those microbes). In other instances the disease or condition causes, or by some mechanism results in, the display of a profile of the microbiota of the GI tract that differs from the normal state. In some contexts this may even be an adaptive response attempting to address the pathological phenotype of the disease or condition.

It is now common place to determine and even quantify the relative amounts of microorganisms in a GI tract sample and to use such profiles to diagnose disease by reference to specific profiles characteristic of a disease state or to rule out a diagnosis by reference to specific profiles characteristic of a normal state (e.g. WO2012080754; WO2011043654). There has however not been a suggestion that the abundance of bacteria from certain taxonomic groupings may be indicative of the likelihood that a subject with IBS will respond to treatment with an IBS intervention diet or faecal microbiota transplant (FMT).

We have now found, surprisingly, that in IBS subjects which are shown to respond to treatment with an IBS intervention diet or FMT, the abundance of bacteria from certain taxonomic groups in faecal samples may be either greater or less than that in subjects non-symptomatic for IBS or IBS subjects which are shown to not respond to treatment with an IBS intervention diet or FMT. Thus, by comparing the amounts of these bacteria in GI tract samples from subjects with IBS with the amounts in corresponding samples from subjects non-symptomatic for IBS, IBS subjects which are likely to respond to treatment with an IBS intervention diet or FMT may be identified and distinguished from those which are unlikely to respond. It follows that alternatively, or additionally, the amounts of these bacteria in GI tract samples from subjects with IBS may be compared with median values for the amounts of these bacteria from GI tract samples from subjects previously shown to be responsive to said treatments and test values greater than a median cut-off value for bacteria from taxonomic groups for which responders show increased amounts compared to non-responders, or test values which are less than a median cut-off value for bacteria from taxonomic groups for which responders show decreased amounts compared to non-responders, are indicative of IBS subjects which are likely to respond to treatment with an IBS intervention diet or FMT.

Thus, as a first aspect the invention provides an in vitro method to determine the likelihood that a subject with irritable bowel syndrome (IBS) will respond to treatment with an IBS intervention diet or faecal microbiota transplant (FMT), said method comprising (i)(a) determining for a test sample from the GI tract of a subject with diarrhoea subtype IBS or mixed subtype IBS to be treated with an IBS intervention diet the amount of bacteria from at least one taxonomic group selected from

*Acinetobacter junii*
*Bacteroides stercosis*
*Bacteroides zoogleoformans*
*Dorea* spp.

*Eubacterium siraeum*
*Clostridium* sp.
*Eubacterium hallii*
*Bacteroides* spp.
Firmicutes
*Veillonella* spp., *Helicobacter* spp., and Clostridia
*Shigella* spp. and *Escherichia* spp., and
*Bacteroides* spp. and *Prevotella* spp.; or (i)(b) determining for a test sample from the GI tract of a subject with constipation subtype IBS to be treated with an IBS intervention diet the amount of bacteria from at least one taxonomic group selected from

*Clostridium methylpentosum*
*Eubacterium siraeum*
*Acinetobacter junii*, and
*Desulfitispora alkaliphila*; or (i)(c) determining for a test sample from the GI tract of a subject with diarrhoea subtype IBS or mixed subtype IBS to be treated with FMT the amount of bacteria from at least one taxonomic group selected from

*Clostridium* sp.
*Eubacterium hallii*
*Bacteroides* spp. and *Prevotella* spp., and
*Dialister invisus*; and (ii)(a) comparing the amount of said bacteria from said at least one taxonomic group with a reference value prepared from at least one sample from the GI tract of at least one subject non-symptomatic for IBS and determining if the amount of said bacteria from said at least one taxonomic group in said test sample differs from, or corresponds to, the reference value; and/or (ii)(b) comparing the amount of said bacteria from said at least one taxonomic group with a cut-off value which has been determined as a median amount of said bacteria in at least one sample from the GI tract of at least one IBS subject with said IBS subtype which has been previously shown to be responsive to said treatment and determining if the amount of said bacteria from said at least one taxonomic group in said test sample is greater than or less than said median cut-off value.

In step (ii)(a), a significant difference between the amount of bacteria from one or more of the above-mentioned taxonomic groups (i.e. target bacteria) in the test sample and the reference value (i.e. the amount of said target bacteria in the reference sample) is indicative that the subject with irritable bowel syndrome (IBS) under test will respond to treatment with an IBS intervention diet or FMT, as appropriate. In other words, if an IBS subject under test is dysbiotic for the target bacteria, this is indicative that the subject will respond to treatment with an IBS intervention diet or FMT, as appropriate. Without wishing to be bound by theory, the extent of any difference in the amounts of said target bacteria (dysbiosis for said target bacteria) may be indicative of the degree of response.

In step (ii)(a), an amount of target bacteria in the test sample corresponding to the reference value is indicative that the subject with IBS under test will not respond to treatment with an IBS intervention diet or FMT, as appropriate. In other words, if an IBS subject under test is normobiotic for the target bacteria, this is indicative that the subject will not respond to treatment with an IBS intervention diet or FMT. Without wishing to be bound by theory, the greater the test and reference values correspond, the greater the likelihood that the subject will not respond.

In step (ii)(b), a test value from said IBS subject for the amount of bacteria from an above-mentioned taxonomic group which is present in increased amounts in IBS subjects of the same subtype which have been previously shown to be responsive to treatment with an IBS intervention diet or FMT, as compared to non-responding IBS subjects of the same subtype, which is greater than a median cut-off value, is indicative that said test subject will respond to treatment with an IBS intervention diet or FMT, as appropriate.

Conversely, in step (ii)(b), a test value from said IBS subject for the amount of bacteria from an above-mentioned taxonomic group which is present in increased amounts in IBS subjects of the same subtype which have been previously shown to be responsive to treatment with an IBS intervention diet or FMT, as compared to non-responding IBS subjects of the same subtype, which is less than a median cut-off value, is indicative that the test subject will not respond to treatment with an IBS intervention diet or FMT, as appropriate.

In step (ii)(b), a test value from said IBS subject for the amount of bacteria from an above-mentioned taxonomic group which is present in decreased amounts in IBS subjects of the same subtype which have been previously shown to be responsive to treatment with an IBS intervention diet or FMT, as compared to non-responding IBS subjects of the same subtype, which is less than a median cut-off value, is indicative that the test subject will respond to treatment with an IBS intervention diet or FMT, as appropriate.

Conversely, in step (ii)(b), a test value from said IBS subject for the amount of bacteria from an above-mentioned taxonomic group which is present in decreased amounts in IBS subjects of the same subtype which have been previously shown to be responsive to treatment with an IBS intervention diet or FMT, as compared to non-responding IBS subjects of the same subtype, which is greater than a median cut-off value, is indicative that the test subject will not respond to treatment with an IBS intervention diet or FMT, as appropriate.

It will be clear to the skilled person that step (ii)(b) as described above amounts to a one-sided analysis of the test values in which the side of importance (i.e. that representing a positive result) is that in the direction of the trend observed in IBS subjects of the same subtype which have been previously shown to be responsive to treatment with an IBS intervention diet or FMT, as appropriate.

The abbreviation "spp." is used herein to denote a plurality of species. In accordance with the invention a reference to a taxonomic group carrying the spp. abbreviation is a reference to a group comprising a plurality of species. This may be considered as a group consisting of bacteria of the same genus. The abbreviation "sp." denotes a single species.

"To determine the likelihood" may be expressed as "to determine the probability" or "to ascertain the probability" or "to assess the probability". As will be clear from the following, the outcomes of these evaluations may be numerical, graphical or illustrative, and in turn each may be qualitative, semi-quantitative or quantitative.

It will also be seen that the method may alternatively be expressed as a method for predicting whether or not a subject with IBS will respond to treatment with an IBS intervention diet or FMT, e.g. whether or not IBS or symptom or complication thereof in a subject with IBS will improve, or is likely to improve, or whether or not development of IBS, or said complication or symptom of IBS will be delayed or prevented, or is likely to be delayed or prevented, following treatment with an IBS intervention diet or FMT. The method may also be expressed as a method to identify, detect, diagnose, classify or stratify IBS patients who are likely to respond to treatment with an IBS intervention diet or FMT.

The invention may also be described more generally as a method for obtaining information useful in, relevant to, or which may assist in, the abovementioned methods.

"Improvement", when used in relation to IBS or the complications and symptoms thereof, is used broadly herein to include any positive change to or reduction in the severity of IBS or the complication or symptom in question or indicator thereof. Thus included, for example, is an improvement in any sign of IBS or complication or symptom thereof, or in any clinically accepted indicator of IBS or complication or symptom thereof in the subject (for example, abdominal pain, diarrhoea, constipation, bloating, abdominal distension, spasm, flatulence, tenesmus and bowel urgency). Improvement does not necessarily require the full eradication of the complication or symptom. The severity of IBS and its symptoms and complications may be monitored by IBS-SSS. In certain embodiments improvement can be considered to be a reduction in a subject's IBS-SSS of at least about 10%, e.g. at least about 15%, 20%, 25%, 30%, 35%, 40%, 45%, 50%, 55%, 60%, 65%, or 70%. In certain embodiments improvement can be considered to be a reduction in a subject's IBS-SSS by at least about 50 points, e.g. at least about 55, 60, 65, 70, 75, 80, 85, 90, 95, 100, 105, 110, 115, 120, 130, 140, or 150 points.

"Delay.", when used in relation to IBS and the complications or symptoms thereof, is intended to include any delay, limitation, or reduction to the onset or development of any effect of IBS, a complication or symptom thereof, or one or more indications thereof, or to the onset or development of IBS, a complication or symptom thereof, or one or more indications thereof, for example relative to the IBS, complication, symptom or indication thereof prior to the treatment.

In contrast "prevention" refers to the absolute prevention of occurrence or development of complications or symptoms of IBS in IBS subjects which do not already display (or have yet to acquire) the complication or symptom in question. Prevention can also be considered to include a reduction to the risk of an IBS patient acquiring or developing the IBS complication or symptom in question.

In certain embodiments the "improvement" or "delay" in accordance with the invention, or the clinical signs thereof, may be seen within 14 days, e.g. 10 days, 7 days, 5 days, 3 days, 2 days, 1 day 18 hrs, 12 hrs or 6 hrs, of commencing treatment with an IBS intervention diet or FMT.

It may be the case that an IBS subject's status as a patient who is likely to respond to treatment with an IBS intervention diet or FMT may change over time. For instance, IBS subjects which are determined to be likely responders may become non-responsive over time. Similarly, IBS subjects which are determined to be likely non-responders may become responsive over time. These transitions between responsive and non-responsive states may occur repeatedly. Accordingly, the methods of the invention may be performed repeatedly in relation to the same subject over time. This may include performing the methods of the invention during or after a subject's treatment with an IBS intervention diet or FMT, e.g. prior to beginning a new course of treatment with an IBS intervention diet or FMT (in order to confirm likelihood of responsiveness). In other instances the methods of the invention may be performed in relation to a subject after an appropriate period of time following a result showing likely non-responsiveness and/or an unsuccessful course of treatment with an IBS intervention diet or FMT. In such embodiments the newly generated results from the patient may also be compared (as defined herein) with previous results.

Thus in certain embodiments the IBS subject is a subject who has not received treatment with an IBS intervention diet or FMT. In other embodiments, the IBS subject is a subject undergoing, or which has received, treatment with an IBS intervention diet or FMT. The IBS subject may be a subject which responded to said treatment or a subject which did not respond to said treatment. In still further embodiments the IBS subject is a subject which has previously been identified as a subject which is likely to respond to treatment with an IBS intervention diet or FMT or a subject which has previously been identified as a subject which is not likely to respond to said treatment.

In certain embodiments, the amounts of bacteria in at least 2, 3, 4, or all, of the above mentioned taxonomic groups are determined and in step (ii)(a) comparison is made with reference values for said taxonomic groups prepared from at least one GI tract sample from at least one subject non-symptomatic for IBS.

In certain embodiments, the amounts of bacteria in at least 2, 3, 4, or all, of the above mentioned taxonomic groups are determined and in step (ii)(b) comparison is made with cut-off values for said taxonomic groups prepared from at least one sample from the GI tract of at least one IBS subject with said IBS subtype and which has been previously shown to be responsive to said treatment.

In certain embodiments, in step (i)(a) said taxonomic group is selected from *Acinetobacter junii, Eubacterium siraeum, Clostridium* sp., *Eubacterium hallii*, Firmicutes, and *Bacteroides* spp. and *Prevotella* spp.

In certain embodiments, in step (i)(b) said taxonomic group is selected from *Acinetobacter junii* and *Eubacterium siraeum*.

In certain embodiments, in step (i)(c) said taxonomic group is selected from *Clostridium* sp., *Eubacterium hallii*, and *Bacteroides* spp. and *Prevotella* spp.

In certain embodiments, in step (i)(a) said taxonomic group is selected from any two or more of *Acinetobacter junii*, Firmicutes, and *Bacteroides* spp. and *Prevotella* spp. or any two or more of *Dorea* spp., *Eubacterium siraeum*, and *Shigella* spp. and *Escherichia* spp. or any two or more of *Eubacterium siraeum*, Firmicutes, and *Bacteroides* spp. and *Prevotella* spp.

In certain embodiments, in step (i)(b) said taxonomic group is selected from any two or more of *Acinetobacter junii, Clostridium methylpentosum* and *Desulfitispora alkaliphila*.

In certain embodiments, in step (i)(c) said taxonomic group is selected from any two or more of *Clostridium* sp., *Eubacterium hallii*, and *Bacteroides* spp. and *Prevotella* spp.

In certain embodiments, the method of the invention comprises step (i)(a) and (ii)(a) and wherein an amount of bacteria in the taxonomic groups *Acinetobacter junii, Bacteroides stercosis, Bacteroides zoogleoformans, Dorea* spp., *Eubacterium siraeum, Clostridium* sp., *Eubacterium hallii* or Firmicutes which is greater than the reference values, or an amount of bacteria in the taxonomic groups *Bacteroides* spp., Firmicutes, *Veillonella* spp., *Helicobacter* spp., and Clostridia, *Shigella* spp. and *Escherichia* spp., or *Bacteroides* spp. and *Prevotella* spp. which is lower than the reference values is indicative that the subject will respond to an IBS intervention diet.

In certain embodiments, the method of the invention comprises step (i)(b) and (ii)(a) and wherein an amount of bacteria in the taxonomic groups *Clostridium methylpento-*

*sum* or *Eubacterium siraeum* which is greater than the reference values, or an amount of bacteria in the taxonomic groups *Acinetobacter junii* or *Desulfitispora alkaliphila* which is lower than the reference values is indicative that the subject will respond to an IBS intervention diet.

In certain embodiments, the method of the invention comprises step (i)(c) and (ii)(a) and wherein an amount of bacteria in the taxonomic groups *Clostridium* sp. or *Eubacterium hallii* which is greater than the reference values, or an amount of bacteria in the taxonomic groups *Bacteroides* spp. and *Prevotella* spp. or *Dialister invisus* which is lower than the reference values is indicative that the subject will respond to FMT.

In certain embodiments, the method of the invention comprises step (i)(a) and (ii)(b) and wherein an amount of bacteria in the taxonomic groups *Acinetobacter junii, Bacteroides stercosis, Bacteroides zoogleoformans, Dorea* spp., *Eubacterium siraeum, Clostridium* sp., *Eubacterium hallii* or Firmicutes which is greater than said median cut-off value for said bacteria, or an amount of bacteria in the taxonomic groups *Bacteroides* spp., Firmicutes, *Veillonella* spp., *Helicobacter* spp., and Clostridia, *Shigella* spp. and *Escherichia* spp., or *Bacteroides* spp. and *Prevotella* spp. which is less than said median cut-off value for said bacteria is indicative that the subject will respond to an IBS intervention diet.

In certain embodiments, the method of the invention comprises step (i)(b) and (ii)(b) and wherein an amount of bacteria in the taxonomic groups *Clostridium methylpentosum* or *Eubacterium siraeum* which is greater than said median cut-off value for said bacteria, or an amount of bacteria in the taxonomic groups *Acinetobacter junii* or *Desulfitispora alkaliphila* which is less than said median cut-off value for said bacteria is indicative that the subject will respond to an IBS intervention diet.

In certain embodiments, the method of the invention comprises step (i)(c) and (ii)(b) and wherein an amount of bacteria in the taxonomic groups *Clostridium* sp. or *Eubacterium hallii* which is greater than said median cut-off value for said bacteria, or an amount of bacteria in the taxonomic groups *Bacteroides* spp. and *Prevotella* spp., or *Dialister invisus* which is less than the median cut-off value for said bacteria is indicative that the subject will respond to FMT.

In further embodiments, the method of the invention comprises steps (ii)(a) and (ii)(b) and the above discussion of the diagnostic outcome of the comparisons between test values and reference values or median cut-off values which may be made in these steps applies mutatis mutandis.

As discussed in detail below, in preferred embodiments the IBS intervention diet is a low (restricted) FODMAP diet or a high FOS diet.

Thus, in certain embodiments the method of the invention comprises step (i)(a) and (ii)(a) and/or (ii)(b), wherein said IBS intervention diet is a low FODMAP diet and wherein said taxonomic group is selected from *Acinetobacter junii, Bacteroides stercosis, Bacteroides zoogleoformans, Dorea* spp., *Eubacterium siraeum, Clostridium* sp., *Eubacterium halli, Bacteroides* spp., Firmicutes, *Veillonella* spp., *Helicobacter* spp., and Clostridia, and *Shigella* spp. and *Escherichia* spp.

Preferably, in these embodiments, in any step (ii)(a) an amount of bacteria in the taxonomic groups *Acinetobacter junii, Bacteroides stercosis, Bacteroides zoogleoformans, Dorea* spp., *Eubacterium siraeum, Clostridium* sp., or *Eubacterium hallii* which is greater than the reference values, or an amount of bacteria in the taxonomic groups *Bacteroides* spp., Firmicutes, *Veillonella* spp., *Helicobacter* spp., and Clostridia, or *Shigella* spp. and *Escherichia* spp. which is lower than the reference values is indicative that the subject will respond to a low FODMAP diet.

Preferably, in these embodiments, in any step (ii)(b) an amount of bacteria in the taxonomic groups *Acinetobacter junii, Bacteroides stercosis, Bacteroides zoogleoformans, Dorea* spp., *Eubacterium siraeum, Clostridium* sp., or *Eubacterium hallii* which is greater than said median cut-off value for said bacteria, or an amount of bacteria in the taxonomic groups *Bacteroides* spp., Firmicutes, *Veillonella* spp., *Helicobacter* spp., and Clostridia, or *Shigella* spp. and *Escherichia* spp. which is less than said median cut-off value for said bacteria is indicative that the subject will respond to a low FODMAP diet.

In other embodiments the method of the invention comprises step (i)(a) and (ii)(a) and/or (ii)(b), wherein said IBS intervention diet is a high FOS diet and wherein said taxonomic group is selected from, *Eubacterium siraeum*, Firmicutes, and *Bacteroides* spp. and *Prevotella* spp.

Preferably, in these embodiments, in any step (ii)(a) an amount of bacteria in the taxonomic groups *Eubacterium siraeum*, Firmicutes, or *Bacteroides* spp. and *Prevotella* spp. which is greater than the reference values is indicative that the subject will respond to a high FOS diet.

Preferably, in these embodiments, in any step (ii)(b) an amount of bacteria in the taxonomic groups *Eubacterium siraeum*, Firmicutes, or *Bacteroides* spp. and *Prevotella* spp. which is greater than said median cut-off value for said bacteria is indicative that the subject will respond to a high FOS diet.

In other embodiments the method of the invention comprises step (i)(b) and (ii)(a) and/or (ii)(b), wherein said IBS intervention diet is a low FODMAP diet and wherein said taxonomic group is selected from *Clostridium methylpentosum, Eubacterium siraeum, Acinetobacter junii*, and *Desulfitispora alkaliphila*.

Preferably, in these embodiments, in any step (ii)(a) an amount of bacteria in the taxonomic groups *Clostridium methylpentosum* or *Eubacterium siraeum* which is greater than the reference values, or an amount of bacteria in the taxonomic groups *Acinetobacter junii* or *Desulfitispora alkaliphila* which is lower than the reference values is indicative that the subject will respond to a low FODMAP diet.

Preferably, in these embodiments, in any step (ii)(b) an amount of bacteria in the taxonomic groups *Clostridium methylpentosum* or *Eubacterium siraeum* which is greater than said median cut-off value for said bacteria, or an amount of bacteria in the taxonomic groups *Acinetobacter junii* or *Desulfitispora alkaliphila* which is less than said median cut-off value for said bacteria is indicative that the subject will respond to a low FODMAP diet.

In still further embodiments the method of the invention comprises step (i)(c) and (ii)(a) or (ii)(b), wherein said subject has diarrhoea subtype IBS and wherein said taxonomic group selected is from *Clostridium* sp., *Eubacterium hallii*, and *Bacteroides* spp. and *Prevotella* spp.

Preferably, in these embodiments, in any step (ii)(a) an amount of bacteria in the taxonomic group *Clostridium* sp., or *Eubacterium hallii* which is greater than the reference values, or an amount of bacteria in the taxonomic group *Bacteroides* spp. and *Prevotella* spp., which is lower than the reference values is indicative that the subject will respond to FMT.

Preferably, in these embodiments, in any step (ii)(b) an amount of bacteria in the taxonomic group *Clostridium* sp., or *Eubacterium hallii* which is greater than said median cut-off value for said bacteria, or an amount of bacteria in the taxonomic group *Bacteroides* spp. and *Prevotella* spp., which is less than said median cut-off value for said bacteria is indicative that the subject will respond to FMT.

In still further embodiments the method of the invention comprises step (i)(c) and (ii)(a) and/or (ii)(b), wherein said subject has mixed subtype IBS and wherein said taxonomic group selected is from *Clostridium* sp., *Bacteroides* spp. and *Prevotella* spp., and *Dialister invisus*.

Preferably, in these embodiments, in any step (ii)(a) an amount of bacteria in the taxonomic group *Clostridium* sp., which is greater than the reference values, or an amount of bacteria in the taxonomic groups *Bacteroides* spp. and *Prevotella* spp., and *Dialister invisus* which is lower than the reference values is indicative that the subject will respond to FMT.

Preferably, in these embodiments, in any step (ii)(b) an amount of bacteria in the taxonomic group *Clostridium* sp., which is greater than said median cut-off value for said bacteria, or an amount of bacteria in the taxonomic groups *Bacteroides* spp. and *Prevotella* spp., and *Dialister invisus* which is less than said median cut-off value for said bacteria is indicative that the subject will respond to FMT.

In accordance with the invention the term "amounts" of bacteria may also be expressed as "levels", "abundance" and the like. These terms are used interchangeably herein.

In embodiments of step (ii)(a) in which the amounts of bacteria from more than one of the above recited taxonomic groups are determined the resulting data/information may be considered to be a pattern or a profile of the selected groups and in these embodiments comparison may be made to a corresponding reference pattern (profile) prepared from at least one sample from the GI tract of at least one subject non-symptomatic for IBS. A significant difference (lack of correlation) between the pattern from the test sample and the reference pattern is indicative that a subject with IBS will respond to treatment with an IBS intervention diet or FMT. Without wishing to be bound by theory, the extent of any difference may be indicative of the degree of response. Likewise, the greater the correlation the less likely the subject will respond to treatment.

In embodiments of step (ii)(b) in which the amounts of bacteria from more than one of the above recited taxonomic groups are determined the resulting data/information may be considered to be a pattern or a profile of the selected groups and in these embodiments comparison may be made to a corresponding reference pattern (profile) prepared from median cut-off values for each taxonomic group which have been determined from at least one sample from the GI tract of at least one IBS subject with the same IBS subtype which has previously been shown to be responsive to said treatment. In these embodiments the comparison may involve determining for one or more of the taxonomic groups tested whether the amount of bacteria from said tested taxonomic group in said test sample is greater than or less than said median cut-off value.

In certain more specific embodiments of the foregoing a score may be attributed to the test profile based on (i) the number of instances in which the test values for the amount of bacteria in the above-mentioned taxonomic groups which are present in increased amounts in IBS subjects with the same IBS subtype and which have been previously shown to be responsive to treatment with an IBS intervention diet or FMT (as appropriate), as compared to non-responding IBS subjects of the same IBS subtype, are greater than the median cut-off values for said bacteria in said responding IBS subjects, and (ii) the number of instances in which the test values for the amount of bacteria in the above-mentioned taxonomic groups which are present in decreased amounts in IBS subjects with the same IBS subtype and which have been previously shown to be responsive to treatment with an IBS intervention diet or FMT (as appropriate), as compared to non-responding IBS subjects with the same IBS subtype, are less than the median cut-off values for said bacteria in said responding IBS subjects. This score is then compared to the number of taxonomic groups tested overall and if the score is equal to or greater than 30%, e.g. equal to or greater than 35%, 40%, 45%, 50%, 55%, 60%, 65%, 70%, 75%, 80%, 85% or 90%, of the number of taxonomic groups tested this is indicative that the subject with IBS will respond to treatment with an IBS intervention diet or FMT.

In other more specific embodiments of the foregoing a score may be attributed to the test profile based on (i) the number of instances in which the test values for the amount of bacteria in the above-mentioned taxonomic groups which are present in increased amounts in IBS subjects with the same IBS subtype and which have been previously shown to be responsive to treatment with an IBS intervention diet or FMT (as appropriate), as compared to non-responding IBS subjects of the same IBS subtype, are less than the median cut-off values for said bacteria in said responding IBS subjects, and (ii) the number of instances in which the test values for the amount of bacteria in the above-mentioned taxonomic groups which are present in decreased amounts in IBS subjects with the same IBS subtype and which have been previously shown to be responsive to treatment with an IBS intervention diet or FMT (as appropriate), as compared to non-responding IBS subjects with the same IBS subtype, are greater than the median cut-off values for said bacteria in said responding IBS subjects. This score is then compared to the number of taxonomic groups tested overall and if the score is equal to or greater than 30%, e.g. equal to or greater than 35%, 40%, 45%, 50%, 55%, 60%, 65%, 70%, 75%, 80%, 85% or 90%, of the number of taxonomic groups tested this is indicative that the subject with IBS will not respond to treatment with an IBS intervention diet or FMT.

The disclosures above which detail which taxonomic groups are indicators of response to an IBS intervention diet or FMT when the amounts thereof are present in the test subject at or above or below median cut-off values applies mutatis mutandis to these embodiments.

In accordance with the invention the amounts of bacteria from the selected taxonomic groups may be determined alongside (together with) the amounts of non-target bacteria or other bacteria which may be later determined to be similarly indicative of an IBS subject's response to an IBS intervention diet or FMT. In other words, data relating to the abundance of the above mentioned target bacteria in a GI tract sample may be obtained or provided with data relating to the abundance of other bacteria.

In this regard the amounts of bacteria in the following taxonomic groups may be determined additionally and compared with reference values for samples from the GI tract of normobiotic subjects or median cut off values for samples from the GI tract of IBS subjects previously shown to be responsive to treatment with an IBS intervention diet or FMT (as appropriate): *Acinetobacter junii*, Firmicutes, *Shigella* spp. and *Escherichia* spp., *Bacteroides fragilis*, Ruminiclostridium, *Streptococcus*, Actinomycetales, *Anaerotruncus*, Clostridiales, and *Eubacterium*.

In certain embodiments of this part of the invention, test values for *Acinetobacter junii*, Firmicutes, *Shigella* spp. and *Escherichia* spp., *Bacteroides fragilis*, Ruminiclostridium, *Streptococcus*, Actinomycetales, *Anaerotruncus*, Clostridiales, and *Eubacterium* which differ from normobiotic reference values are indicative that a subject with IBS will respond to treatment with a low FODMAP diet. Conversely, test values for *Acinetobacter junii*, Firmicutes, *Shigella* spp. and *Escherichia* spp., *Bacteroides fragilis*, Ruminiclostridium, *Streptococcus*, Actinomycetales, *Anaerotruncus*, Clostridiales, and *Eubacterium* which correspond to normobiotic reference values are indicative that a subject with IBS will not respond to treatment with a low FODMAP diet.

In certain embodiments of this part of the invention, test values for *Acinetobacter junii*, *Bacteroides fragilis*, Ruminiclostridium. *Streptococcus* and *Eubacterium* which are greater than normobiotic reference values, or which are greater than median cut-off values from IBS subjects previously shown to be responsive to treatment with a low FODMAP diet, are indicative that a subject with IBS will respond to treatment with a low FODMAP diet.

In certain embodiments of this part of the invention, test values for Firmicutes, *Shigella* spp. and *Escherichia* spp., Actinomycetales, *Anaerotruncus*, and Clostridiales which are less than normobiotic reference values, or which are less than median cut-off values from IBS subjects previously shown to be responsive to treatment with a low FODMAP diet, are indicative that a subject with IBS will respond to treatment with a low FODMAP diet.

In certain embodiments of this part of the invention, test values for *Acinetobacter junii*, *Bacteroides fragilis*, Ruminiclostridium. *Streptococcus* and *Eubacterium* which are less than median cut-off values from IBS subjects previously shown to be responsive to treatment with a low FODMAP diet, are indicative that a subject with IBS will not respond to treatment with a low FODMAP diet.

In certain embodiments, test values for Firmicutes, *Shigella* spp. and *Escherichia* spp., Actinomycetales, *Anaerotruncus*, and Clostridiales which are greater than median cut-off values from IBS subjects previously shown to be responsive to treatment with a low FODMAP diet, are indicative that a subject with IBS will not respond to treatment with a low FODMAP diet.

The GI tract, also referred to as the digestive tract or alimentary canal (and which terms may be used interchangeably with GI tract) is the continuous series of organs beginning at the mouth and ending at the anus. Specifically this sequence consists of the mouth, the pharynx, the oesophagus, the stomach, the duodenum, the small intestine, the large intestine and the anus. These organs can be subdivided into the upper GI tract, consisting of the mouth, pharynx, oesophagus, stomach, and duodenum, and the lower GI tract, consisting of the jejunum, the ileum (together the small intestine), the cecum, the colon, the rectum (together the large intestine) and the anus.

A GI tract sample of use in accordance with the invention may include, but is not limited to, any fluid or solid taken from the lumen or surface of the GI tract or any sample of any of the tissues that form the organs of the GI tract. Thus the sample may be any luminal content of the GI tract (e.g. stomach contents, intestinal contents, mucus and faeces/stool, or combinations thereof) as well as samples obtained mechanically from the GI tract e.g. by swab, rinse, aspirate or scrape of a GI tract cavity or surface or by biopsy of a GI tract tissue/organ. Faecal samples are preferred. The sample can also be obtained from part of a GI tract tissue/organ which has been removed surgically. The sample may be a portion of the excised tissue/organ. In embodiments where the sample is a sample of a GI tract tissue/organ the sample may comprise a part of the mucosa, the submucosa, the muscularis externa, the adventitia and/or the serosa of the GI tract tissue/organ. Such tissue samples may be obtained by biopsy during an endoscopic procedure. Preferably the sample is obtained from the lower GI tract, i.e. from the jejunum, the ileum, the cecum, the colon, the rectum or the anus. More preferably the sample is a mucosal or luminal sample. Faecal samples may be collected by the swab, rinse, aspirate or scrape of the rectum or anus or, most simply, the collection of faeces during or after defecation.

The sample may be used in accordance with the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above mentioned samples. The term "sample" also includes preparations of the above mentioned samples in which the RNA of which, including the 16S rRNA, has undergone reverse transcription. Further included is the product of the microbial culture of said sample.

The purification may be slight, for instance amounting to no more than the concentration of the solids, or cells, of the sample into a smaller volume or the separation of cells from some or all of the remainder of the sample. Representative cell isolation techniques are described in WO98/51693 and WO01/53525.

In certain embodiments a preparation of the nucleic acid from the above mentioned samples, preferably a preparation in which the nucleic acids have been labelled, is used in accordance with the invention. Such preparations include reverse transcription products and/or amplification products of such samples or nucleic acid preparations thereof. It may be advantageous if the predominant nucleic acid of the nucleic acid preparation is DNA. These preparations include relatively pure or partially purified nucleic acid preparations.

Techniques for the isolation of nucleic acid from samples, including complex samples, are numerous and well known in the art and described at length in the literature. The techniques described in WO98/51693 and WO01/53525 can also be employed to prepare nucleic acids from the above mentioned samples.

The method of the invention may include a step of sample collection and/or sample processing and/or culture, in particular a step of nucleic acid amplification, e.g. genomic nucleic acid amplification, in particular the amplification of nucleic acid carrying nucleotide sequences characteristic of a microorganism or group of microorganisms.

Unless context dictates otherwise, the term "corresponding sample" is used herein to refer to samples of the same type which have been obtained from different subjects and/or at different times in essentially the same way and to which any substantive processing or handling thereof has taken place in essentially the same way.

Methods for determining the amount of bacteria from a target taxonomic group in a GI tract sample include, but are not limited to, nucleic acid analysis (e.g. nucleic acid sequencing approaches, oligonucleotide hybridisation probe based approaches, primer based nucleic acid amplification approaches), antibody or other specific affinity ligand based approaches, proteomic and metabolomic approaches. Preferably the analysis of the sample will be by nucleic acid sequence analysis and may take the form of a sequencing technique. The Sanger dideoxynucleotide sequencing method is a well-known and widely used technique for sequencing nucleic acids. However more recently the so-called "next generation" or "second generation" sequencing approaches (in reference to the Sanger dideoxynucleotide method as the "first generation" approach) have become widespread. These newer techniques are characterised by high throughputs, e.g. as a consequence of the use of parallel, e.g. massively parallel sequencing reactions, or through less time-consuming steps. Various high throughput sequencing methods provide single molecule sequencing and employ techniques such as pyrosequencing, reversible terminator sequencing, cleavable probe sequencing by ligation, non-cleavable probe sequencing by ligation, DNA nanoballs, and real-time single molecule sequencing e.g. nanopore based sequencing.

Nucleic acid sequence analysis may also preferably take the form of an oligonucleotide hybridisation probe based approach in which the presence of a target nucleotide sequence is confirmed by detecting a specific hybridisation event between a probe and its target. In these approaches the oligonucleotide probe is often provided as part of a wider array, e.g. an immobilised nucleic acid microarray. Preferably, the oligonucleotide probe sets and associated methods of WO 2012/080754, WO 2011/043654, Vebo et al., Clin Vaccine Immunol, 2011, Vol; 18(8):1326-35, and Casén, C., et al, Alimentary Pharmacology and Therapeutics, 42(1):71-83) and/or the GAmap™ (Genetic Analysis AS, Norway) may be used to prepare microbiota profiles in accordance with the present invention.

Data generated using the above mentioned methods may be analysed using various techniques, from the most basic visual representation (e.g. relating to signal intensity) to more complex data manipulation, which may be quantified and expressed mathematically, to determine the amount of bacteria from a target taxonomic group in the GI tract sample and/or to compare the data generated initially or following some degree of data processing from the test sample to the reference values from the non-symptomatic subject, and/or cut-off values from IBS subjects which are shown to not respond to treatment with an IBS intervention diet or FMT (as appropriate). Conveniently, the raw data thus generated may be manipulated by data processing and statistical methods, particularly normalising and standardising the data. The skilled man would be aware of suitable statistical techniques to use. Preferably the statistical technique will provide a "P value" as an indication that the trend being observed is not a random trend. A statistically significant result, i.e. a result that is not attributable to random variation when compared to its control, will have a P value of <0.05, preferably <0.01, <0.005 or <0.001. Merely by way of example, suitable techniques for measuring statistical significance in the methods of the invention are ANOVA, Mann-Whitney-Wilcoxon (MWW) Test, Kruskal-Wallis Test and Tukey's Honestly Significant Differences (HSD) Test. The prediction methods include Discriminant Analysis methods, Logistic regression, Soft Independent Modelling of Class Analogy based on Principal Component Analysis, Partial Least Squares Discriminant Analysis, and so on. Many others would be familiar to the skilled man. In some embodiments a permutation test might be appropriate, e.g. that described by Langsrud (2002, Journal of the Royal Statistical Society Series D 51, 305-317) and in Vebo et al. (supra) and Casén, et al (supra). The parallel analysis of the amounts of bacteria in a sample may be described as differential abundance analysis or differential abundant feature detection. Any suitable technique may be used in accordance with the invention. In this regard numerous software tools for such analyses and the comparison of such analyses between reference and test samples are publicly available. Merely by way of example, mention may be made of DESeq, MEGAN, STAMP, metagenomeSeq, Myrna, RADs, metaDprof, mcaGUI, and METAGENassist. In other embodiments supervised learning techniques may be applied to the data. Merely by way of example, mention may be made of support vector machines (SVM), artificial neural networks, naïve Bayes classifier, decision tree learning, nearest neighbour algorithms (kNN), random forests, Bayesian statistics and Bayesian machine learning.

In accordance with the invention said reference value (or patterns or profiles) prepared from at least one sample from the GI tract of at least one subject non-symptomatic for IBS are values (patterns/profiles) prepared in essentially the same way as the test values/patterns/profiles (the amount of bacteria in the target taxonomic group, or patterns/profiles thereof), preferably using the same equipment at the same settings and with the same experimental conditions, from a GI tract sample from the essentially the same part of the GI tract as the sample from the test patient (or vice versa). In other words a corresponding sample. In convenient embodiments the test and reference samples are faecal samples. In further embodiments the reference samples are obtained by the same means and processed and stored in essentially the same way as the test samples (or vice versa). In preferred embodiments the reference value (pattern/profile) may be obtained from more than one (generally a cohort of) subjects non-symptomatic for IBS and said value is presented as an average value (e.g. mean) or model pattern/profile. The features of the preparation of said median cut-values (or patterns or profiles) from at least one sample from the GI tract of at least one IBS subject with the same IBS subtype as the test subject which has been previously shown to be responsive to treatment with an IBS intervention diet or FMT should be interpreted analogously.

A subject which is non-symptomatic for IBS is a subject which would not be diagnosed as having IBS, in particular in accordance with the Rome III criteria. Such subject may display one or more symptoms of IBS, but IBS as an underlying cause like have been ruled out. Ideally, a subject which is non-symptomatic for IBS is a subject in which GI tract function is essentially "normal"/"healthy", i.e. not dysfunctional or showing any evidence of dysfunction. In certain embodiments the subject does not have GI tract dysbiosis, e.g. as determined by the GAmap™ test. More generally the subject may be a "normal" or "healthy" subject essentially free of serious illness or disease or other medical conditions, or at least is a subject that does not have observable or detectable symptoms of any recognised serious illness or disease. In other embodiments a normal or healthy subject will be free of all illness or disease or other medical conditions, or at least does not have observable or detectable symptoms of any recognised illness or disease. Preferably these references to illness, disease or medical condition are references to an illness, disease or medical condition of the GI tract.

Comparing the test value for the amount of bacteria from a target taxonomic group (or profile/pattern thereof, as appropriate) with the reference value (or profile/pattern) and assessing any difference (or lack of correspondence) or correspondence between the two may be a qualitative, semi-quantitative or quantitative process. In the context of the present invention, to correspond to a reference value (or profile/pattern thereof) is to be substantially, e.g. essentially, the same as (or to be similar to) a reference value (or pattern/profile thereof). To differ should be interpreted consistently with this. Thus, a test value (or pattern/profile) corresponds to the reference if it is substantially the same, or if it is similar or equivalent to, or matches or fits, the reference e.g. it is statistically similar or statistically equivalent. Thus, a test value (or pattern/profile) differs to the reference if it is not substantially the same, or if it is not similar or equivalent to, or does not match or fit, the reference e.g. it is not statistically similar or statistically equivalent. Thus, the steps of comparing the test and reference values (or pattern/profile) and determining whether or not they correspond (or differ) may be performed using mathematical, or statistical techniques (e.g. using predictive models and algorithms which have been prepared from prior obtained reference values), and generally this will be implemented by software (i.e. it will be performed using a computer, i.e. virtually). Statistical or mathematical methods for performing such a comparison and determination of correspondence are well known and widely available in the art. Thus, it will also clearly be understood that it is not necessary in each case to prepare a reference value or pattern or model (i.e. for each test).

In one embodiment the amount of bacteria from a target taxonomic group (or profile/pattern thereof, as appropriate) in the test and reference samples may be expressed as a visual representation and in which case the test and reference values may be compared visually, or with analogous technologically assisted means, and correspondence (or difference) between the test and reference values is then estimated.

In another embodiment correspondence (or difference) between a test and a reference value (or pattern/profile) may be analysed by applying said test value (or pattern/profile) to a mathematical model generated using the reference value(s) (or pattern(s)/profile(s)). Such a mathematical model may be used to determine whether a test value fits, or matches, a reference value. Mathematical methods for generating such a model are well known, and may, for instance, be prepared using linear regression techniques. Accordingly, such an analysis may be performed using a linear regression predictive model prepared from a plurality of reference values (or patterns/profiles).

In embodiments in which amounts of bacteria from two taxonomic groups are determined, correspondence between a test and a reference pattern/profile is analysed via representation of the test and reference patterns as single points in a two dimensional Cartesian coordinate system said points having coordinates which are the values for the amounts of bacteria in the two target taxonomic groups, e.g. as a 2D scatter plot (graph), but this is not essential. Collocation of the data points suggests that the subject will be non-responsive to treatment. A lack of collocation suggests that the subject will be responsive to treatment.

Collocation of the test data point with a reference data point may be considered to occur if the test data point is within an area defined as having the reference data point at its centre and having a length and a width (x and y dimensions) running through said centre point which are equal to or less than 50% of the value of the relevant coordinate in the reference data point (i.e. the amount of bacteria in the target taxonomic group which is in the same dimension as the length or width of the area). In further embodiments, said length and/or width of the area is equal to or less than a 40%, e.g. equal to or less than a 30%, 20%, 10% or 2% the relevant coordinate.

In other embodiments in which amounts of bacteria from three taxonomic groups are determined, correspondence between a test and a reference pattern/profile is analysed via representation of the test and reference patterns as single points in Euclidean space having coordinates which are the values for the amounts of bacteria in the three target taxonomic groups, e.g. as a 3D scatter plot (graph), but this is not essential. Collocation of the data points suggests that the subject will be non-responsive to treatment. A lack of collocation suggests that the subject will be responsive to treatment.

Collocation of the test data point with a reference data point may be considered to occur if the test data point is within an Euclidean volume defined as having the reference data point at its centre and edges (or boundaries) running in the same three dimensions as the three coordinates of the reference data point, wherein the length of said edges are equal to or less than 50% of the relevant coordinate making up the reference data point (i.e. the amount of bacteria in the target taxonomic group which is in the same dimension as the edge in question). In further embodiments, said edge length is equal to or less than a 40%, e.g. equal to or less than a 30%, 20%, 10% or 2% the relevant coordinate.

In certain embodiments the single test data point is compared to a plurality of reference data points and collocation may be considered to occur if the test data point is substantially, e.g. essentially, at or within the outermost boundaries formed by the cluster of reference points. This may be determined by any convenient cluster analysis technique or algorithm (which may also be referred to as a cluster algorithm), which may be 2D or 3D, for example hierarchical cluster analysis using Euclidean distance as a distance measure and an "average" tree building method Correspondence between a single test and a single reference value can be considered to occur if the test value is equal to or less than a 25% positive or negative deviation from the reference value. In further embodiments, said positive or negative deviation is equal to or less than 20%, e.g. equal to or less than a 15%, 10%, 5% or 1%.

An IBS subject (subject with IBS, subject suffering from IBS) is a subject which has been diagnosed as having IBS, in particular in accordance with the Rome III criteria. IBS subjects may be subtyped based on their predominant digestive symptom as diarrhoea, constipation or mixed subtypes. The severity of the subject's IBS symptoms may be expressed in the form of the IBS-Symptom Severity Score (IBS-SSS; as defined in Francis C. Y., Aliment Pharmacol Ther. 1997 April; 11(2):395-402). The maximum achievable score of this inventory is 500 points, allowing grading of symptom severity as follows: mild (75-175 points), moderate (175-300 points) and severe (>300 points). In accordance with the invention, an IBS subject which responds to an intervention (e.g. a dietary intervention or FMT) may be defined as being a subject in which there is an at least 30%, e.g. at least 40%, 45%, 50%, 55%, 60%, 65% or 70%, in particular at least 50%, reduction in total IBS-SSS from baseline to post intervention. Alternatively, in accordance with the invention, an IBS subject which responds to an intervention (e.g. a dietary intervention or FMT) may be defined as being a subject in which there is an at least 50, e.g. at least 60, 70, 80, 90, 100, 110, 120, 130, 140 or 150, in particular at least 100, point reduction in total IBS-SSS from baseline to post intervention.

Median cut-off values are derived from a plurality of values for the amount of bacteria in a chosen taxonomic group of the invention as recited above from at least one GI tract sample from at least one IBS subject (of the same IBS subtype as the test subject, if appropriate) which is known to be responsive to treatment with an IBS intervention diet or FMT, as appropriate, as defined herein. Preferably median cut-off values are derived from values obtained from a plurality of samples from at least one IBS subject (of the same IBS subtype as the test subject, if appropriate) which is known to be responsive to treatment with an IBS intervention diet or FMT, as appropriate, as defined herein. Preferably median cut-off values are derived from values obtained from at least one sample from at a plurality of IBS subjects (of the same IBS subtype as the test subject, if appropriate) which are known to be responsive to treatment with an IBS intervention diet or FMT, as appropriate, as defined herein. Most preferably median cut-off values are derived from values obtained from a plurality of samples from a plurality of IBS subjects (of the same IBS subtype as the test subject, if appropriate) which are known to be responsive to treatment with an IBS intervention diet or FMT, as appropriate, as defined herein.

The comparison between test values and median cut-off values may be achieved by any convenient means. In certain embodiments the comparison will involve steps to determine whether or not the test value is statistically significantly greater (or less) than the median cut-of value. Thus, the comparison will involve mathematical (statistical) techniques, and this will generally be implemented by software (i.e. it will be performed using a computer, i.e. virtually). Statistical or mathematical methods for performing such a comparisons and determinations are well known and widely available in the art, e.g. those described above. Thus, it will also clearly be understood that it is not necessary in each case to prepare a median cut-off value or pattern or model (i.e. for each test).

In other embodiments in which the amounts of bacteria from more than one taxonomic group are determined, a test pattern/profile can be considered to correspond to a reference pattern/profile if 2 or more, e.g. all, of the test values are equal to or less than a 25% positive or negative deviation from the corresponding reference values. In further embodiments, said positive or negative deviation is equal to or less than 20%, e.g. equal to or less than a 15%, 10%, 5% or 1%.

An IBS intervention diet may be any diet which can or which has been shown to (i) treat (improve) IBS or a symptom or complication thereof in a subject with IBS, i.e. to have a positive (beneficial) effect on the GI tract of an IBS subject, specifically the GI tract microbiota, or other symptoms or complications of IBS (e.g. reducing severity thereof) or (ii) prevent of delay the development of IBS or a complication or symptom thereof in a subject. This would include diets rich in prebiotics, diets restricted in prebiotics, and diets rich in probiotics. Important examples of such diets include low FODMAP (also referred to herein as restricted FODMAP) and high FOS (also referred to as FOS rich). These diets are described and defined in Slavin J. Nutrients. 2013 April; 5(4): 1417-1435 and Gearry R. B et al, JCC 2008.09.004 8-14) The skilled man would recognise such diets immediately and be able to devise such diets without undue burden from his common knowledge or by referring to the literature, e.g. Slavin and Gearry, supra.

Faecal microbiota transplant (also referred to as human probiotic infusion, faecal bacteriotherapy, microbiota restoration therapy faecal transfusion, faecal transplant, stool transplant and faecal enema) refers to a procedure in which faecal matter is collected from a selected donor and administered to a recipient after some degree of sample processing. In some techniques the faecal matter is mixed with saline or other pharmaceutically acceptable solution, strained, and placed in a patient by colonoscopy, endoscopy, sigmoidoscopy, or enema. In other techniques solid matter is separated from the faecal matter and lyophilised prior to administration by colonoscopy, endoscopy, sigmoidoscopy, enema, rectal catheter or orally. Preferably FMT is as described in Francis C. Y., Aliment Pharmacol Ther. 1997 April; 11(2): 395-402 or Betz, C., et al, Z Gastroenterol., 2013, 51(10): 1171-6).

The subject may be any human or non-human animal subject, but more particularly may be a vertebrate, e.g. a mammal, including livestock and companion animals. Preferably the subject is a human, in which case the term "patient" may be used interchangeably with the term "subject". The subject may be of any age, e.g. an infant, a child, a juvenile, an adolescent or an adult, preferably an adult. In humans, an adult is considered to be of at least 16 years of age and an infant to be up to 2 years of age. In certain embodiments the subject will be an infant, in others it will be a child or an adult. An IBS subject (or patient) is with a subject (or patient) with IBS and the terms may be used interchangeably herein. The subject may be determined to have (diagnosed as having) IBS or a subtype thereof by apply the Rome III criteria as described above. The method of the invention may therefore include a step in which the test subject is determined to have (diagnosed as having) IBS.

The method of this aspect of the invention is an in vitro method insofar as it is performed on a sample which has been obtained, or isolated, from the GI tract of a subject. In other words the method is not performed in vivo or is not performed on the body of the subject. Nevertheless, in more specific aspects the method may further include a step in which the sample is obtained or isolated from the subject, preferably non-surgically or non-invasively. Thus, in this aspect, the treatment of the patient (i.e. the step of treating the subject with an IBS intervention diet or FMT) is not part of the method. Thus for example, references to outcomes following treatment are intellectual references to possible outcomes and the step of treating the subject with an IBS intervention diet, or administering FMT, is not part of the methods of this aspect of the invention. However, it may be the case that such treatments are administered to the patient following the method as described in this aspect.

Thus, in a further particular aspect, a method of the invention may further comprise administering an IBS intervention diet or FMT to the subject if it is determined that the subject is likely to respond thereto (and conversely, not administering an IBS intervention diet or FMT to the subject if it is determined that the subject is not likely to respond thereto).

Thus, according to this aspect, the invention may provide a method of treatment of a subject with IBS wherein it is first determined by the method defined above that the subject may respond to (i.e. is likely to respond to) administration of an IBS intervention diet or FMT, and the method further (or subsequently) comprises administering to the subject so determined to be a likely responder an effective amount of an IBS intervention diet or FMT alginate oligomer, i.e. treating said subject with an IBS intervention diet or FMT.

This aspect of the invention further provides a method of treatment of a subject with IBS, said method comprising administering to the subject an effective amount of an IBS intervention diet or FMT (or treating said subject with an IBS intervention diet or FMT), wherein said subject has been determined to be a likely responder to treatment with an IBS intervention diet or FMT by the method defined above for determining likelihood of response.

The word "corresponding" is used to convey the concept that the subject to which the term is applied is the same as another instance of that subject. Thus the essential features that define that subject are shared by the other subject even though precise details may be unique. Alternative terms could be "matching", "analogous", agreeing", "equivalent" or "same as".

In certain embodiments the "improvement" or "delay" in accordance with the invention, or the clinical signs thereof, may be seen within 14 days, e.g. 10 days, 7 days, 5 days, 3 days, 2 days, 1 day 18 hrs, 12 hrs or 6 hrs, of commencing treatment with the IBS intervention diet or FMT as appropriate.

In certain embodiments the preventive effects of treatment with the IBS intervention diet or FMT, as appropriate, in accordance with the invention are maintained for the duration of the subject's treatment.

Although the invention has been described herein in the context of IBS subjects and their response to IBS intervention diets or FMT, it will be appreciated that the underlying concept of the invention will be more broadly applicable both in terms of the medical indication of the target subject and the therapies of interest.

In this regard and as alluded to above, many diseases and conditions, or stages thereof, are believed to be associated with perturbations in the microbiota of the GI tract, or regions thereof. Diseases and conditions affecting the GI tract are very likely to result in microbiota profiles that vary from the normal state, e.g. Inflammatory Bowel Disease (IBD), Crohn's Disease (CD), Ulcerative Colitis (UC), Irritable Bowel Syndrome (IBS), small bowel bacterial overgrowth syndrome and GI tract cancers (e.g. cancer of the mouth, pharynx, oesophagus, stomach, duodenum, jejunum, ileum, cecum, colon, rectum or anus) and evidence also exists of links between GI tract microbiota profiles and diseases and conditions that are considered to be unrelated to the GI tract, for instance breast cancer; ankylosing spondylitis; non-alcoholic steatohepatitis; the atopic diseases, e.g. eczema, asthma, atopic dermatitis, allergic conjunctivitis, allergic rhinitis and food allergies; metabolic disorders, e.g. diabetes mellitus (type 1 and type 2), obesity and metabolic syndrome; neurological disorders, e.g. depression, multiple sclerosis, dementia, and Alzheimer's disease; autoimmune disease (e.g. arthritis); malnutrition; chronic fatigue syndrome and autism. It is believed that such perturbations of the GI tract microbiota profile (in terms of relative amounts and/or diversity), which may be considered to equate to an imbalance in the GI tract microbiota, contribute to these diseases, either by causing the diseases or contributing to their progression. It is also believed that many more diseases will be found to have causal links to perturbations of the GI tract microbiota profile. The precise mechanism behind this causation is not well understood. It is clear that perturbation of the microbiota of the GI tract results in the underpopulation of certain microbes and/or the overpopulation of others and/or reductions in diversity and this causes a shift, or imbalance, in the relative activities of each microbe population. It is believed that this shift in microbial activities causes a reduction in beneficial effects (e.g. synthesis of vitamins, short-chain fatty acids and polyamines, nutrient absorption, inhibition of pathogens, metabolism of plant compounds) to occur and/or an increase in deleterious effects (secretion of endotoxins and other toxic products) to occur with consequent overall negative effects on the host's overall physiology. These effects can then manifest as illness and disease, e.g. those recited above.

These diseases and conditions have a plethora of different therapeutic treatments, some of which target the GI tract and the microbiota therein, e.g. the administration of antibiotics, antibody therapy, anti-inflammatoires, immunomodulators (immune suppressors or immunostimulators), probiotics or prebiotics and so on. Specifically in the context of IBS and all its subtypes, treatment may include antibiotics (e.g. rifaximin), linaclotide and eluxadoline. In light of the present invention it is therefore reasonable to expect that the amounts of bacteria from certain taxonomic groups would be indicative of responders and/or non-responders to such treatments. Thus the concepts of the invention could be applied mutatis mutandis to such contexts.

(FODMAP response in IBS subgroup Diarrhoea). Light grey=responders, Dark grey-non-responders.

Figure 1:
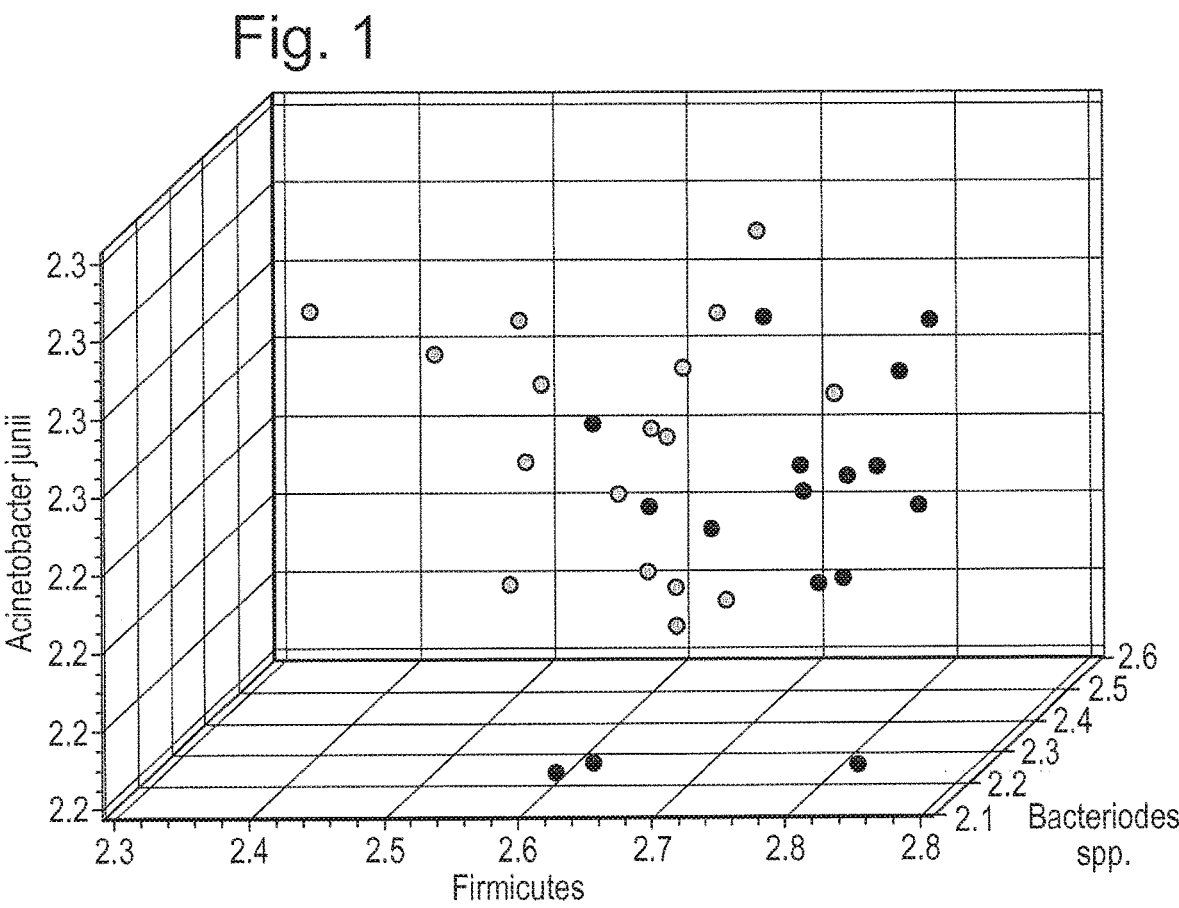
FIG. 1 shows a 3D classification plot using *Bacteroides* spp., *Acinetobacter junii* and Firmicutes results from Example 1 Study 1 (low FODMAP diet response in IBS subgroup Diarrhoea). Light grey=responders, Dark grey=non-responders.
Figure 2:
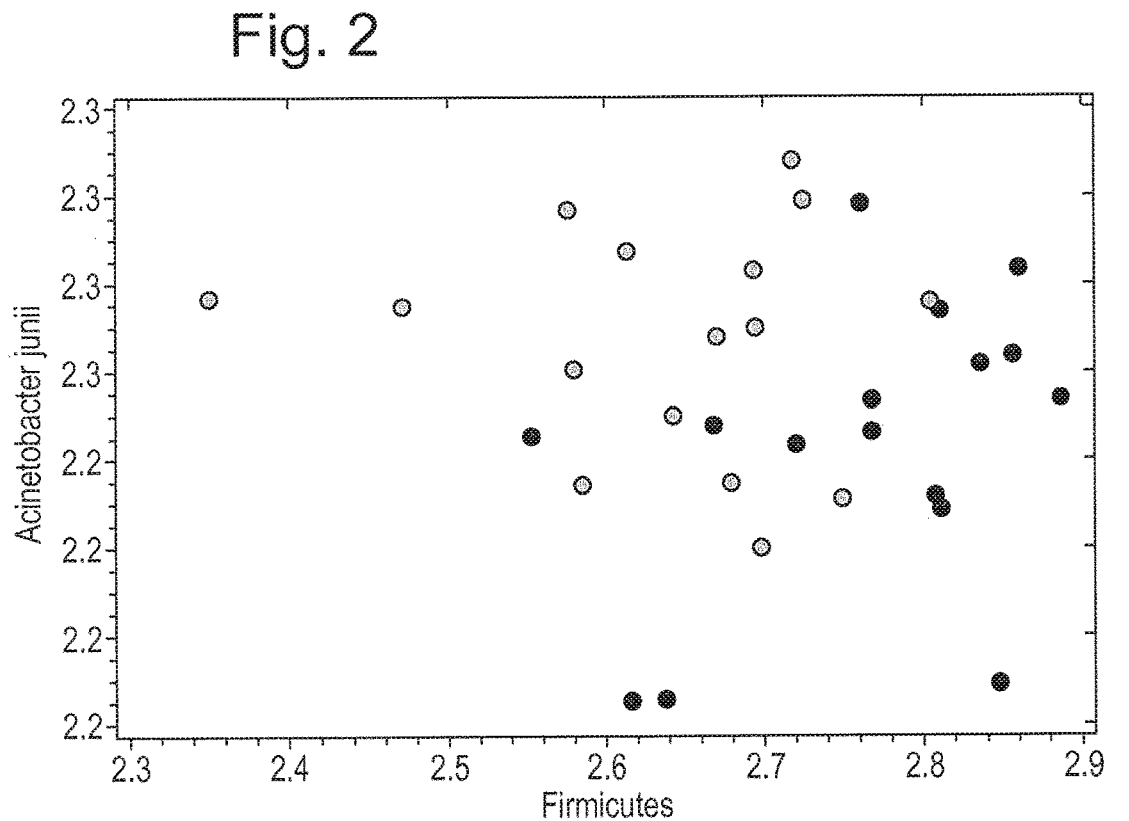
FIG. 2 shows a 2D classification plot using *Acinetobacter junii* and Firmicutes results from Example 1 Study 1 (low FODMAP diet response in IBS subgroup Diarrhoea). Light grey=responders, Dark grey=non-responders.
Figure 3:
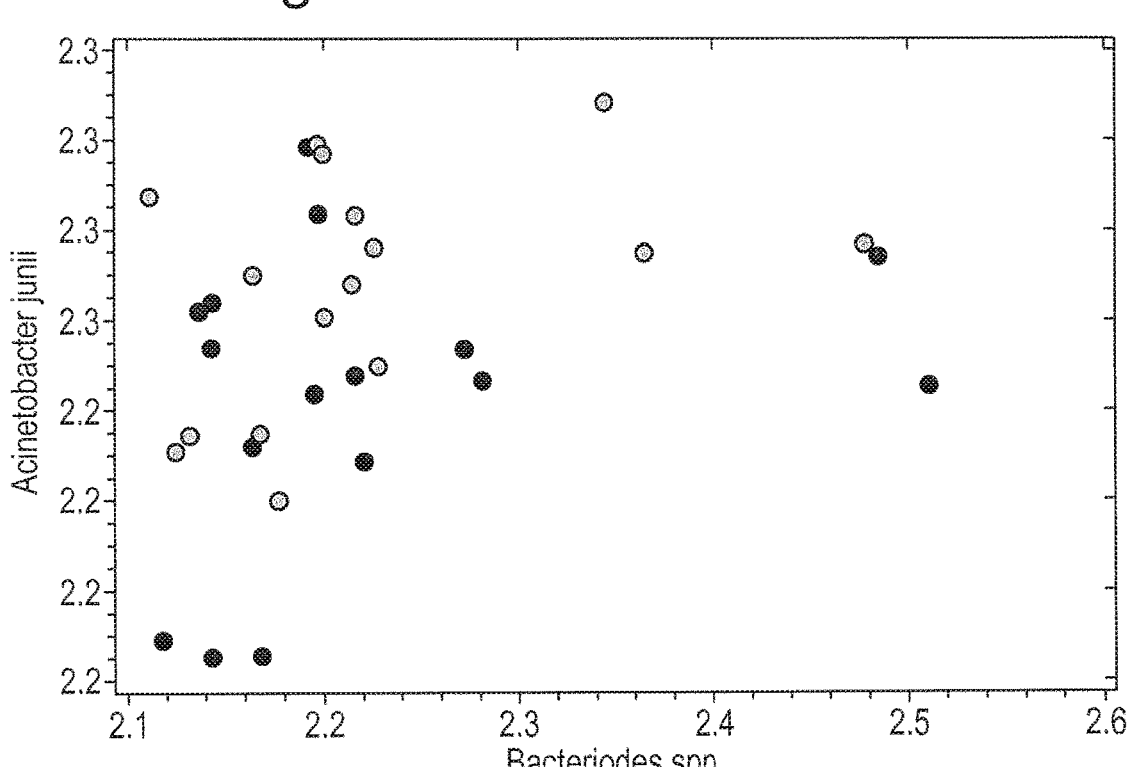
FIG. 3 shows a 2D classification plot using *Acinetobacter junii* and *Bacteroides* spp. results from Example 1 Study 1 (low FODMAP diet response in IBS subgroup Diarrhoea). Light grey=responders, Dark grey=non-responders.
Figure 4:
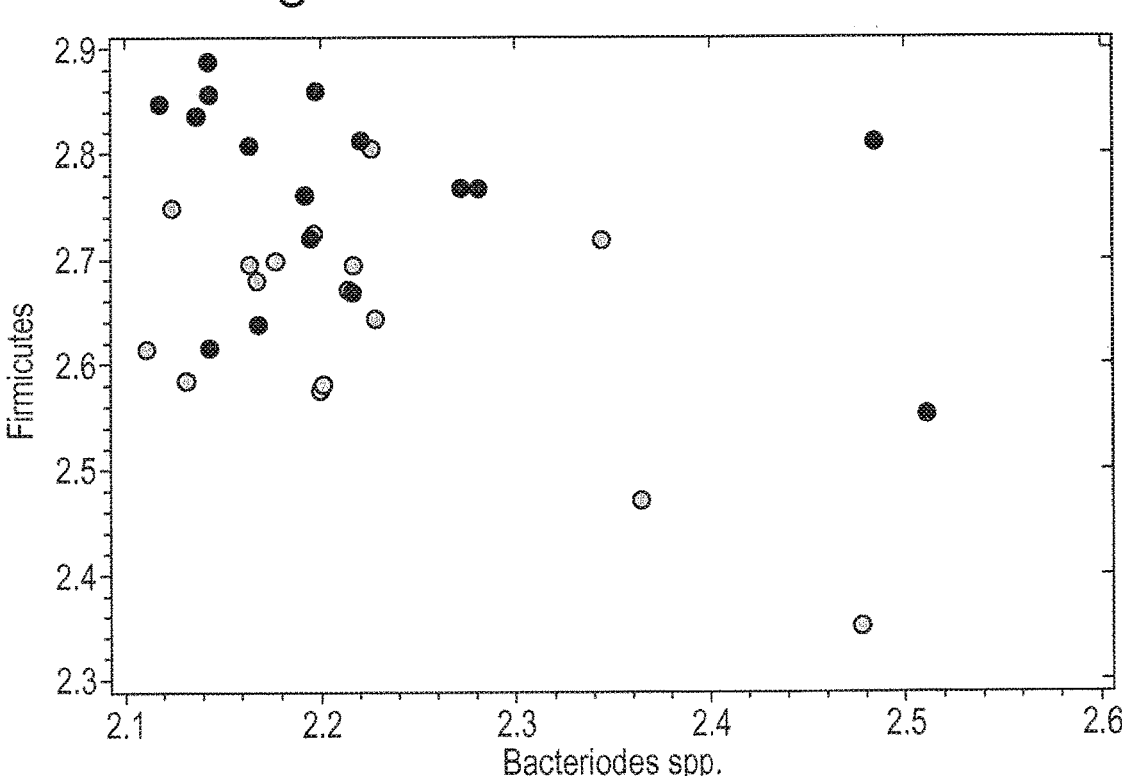
FIG. 4 shows a 2D classification plot using Firmicutes and *Bacteroides* spp. results from Example 1 Study 1 (low FODMAP diet response in IBS subgroup Diarrhoea). Light grey=responders, Dark grey=non-responders.
Figure 5:
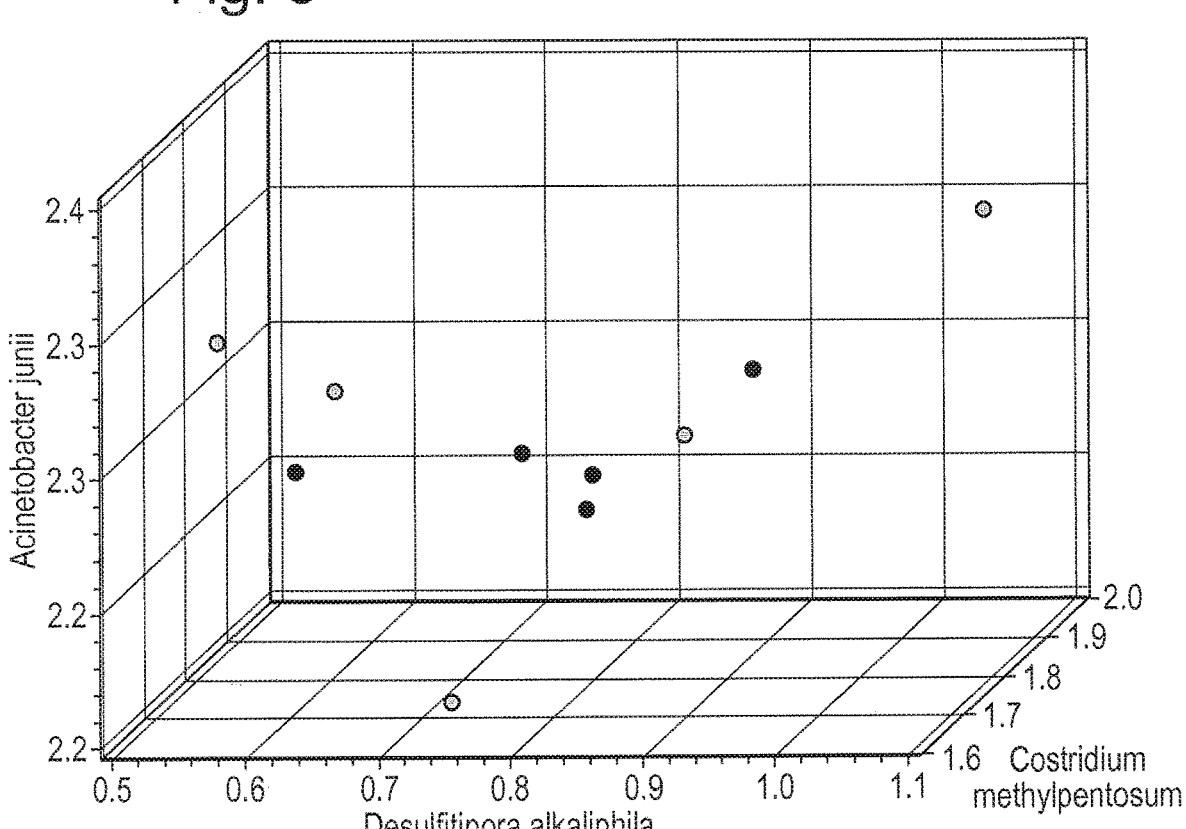
FIG. 5 shows a 3D classification plot using *Acinetobacter junii, Costridium methylpentosum* and *Desulfitispora alkaliphila* results from Example 1 Study 1 (low FODMAP diet response in IBS subgroup) Light grey=responders, Dark grey-non-responders (accuracy 80%).
Figure 6:
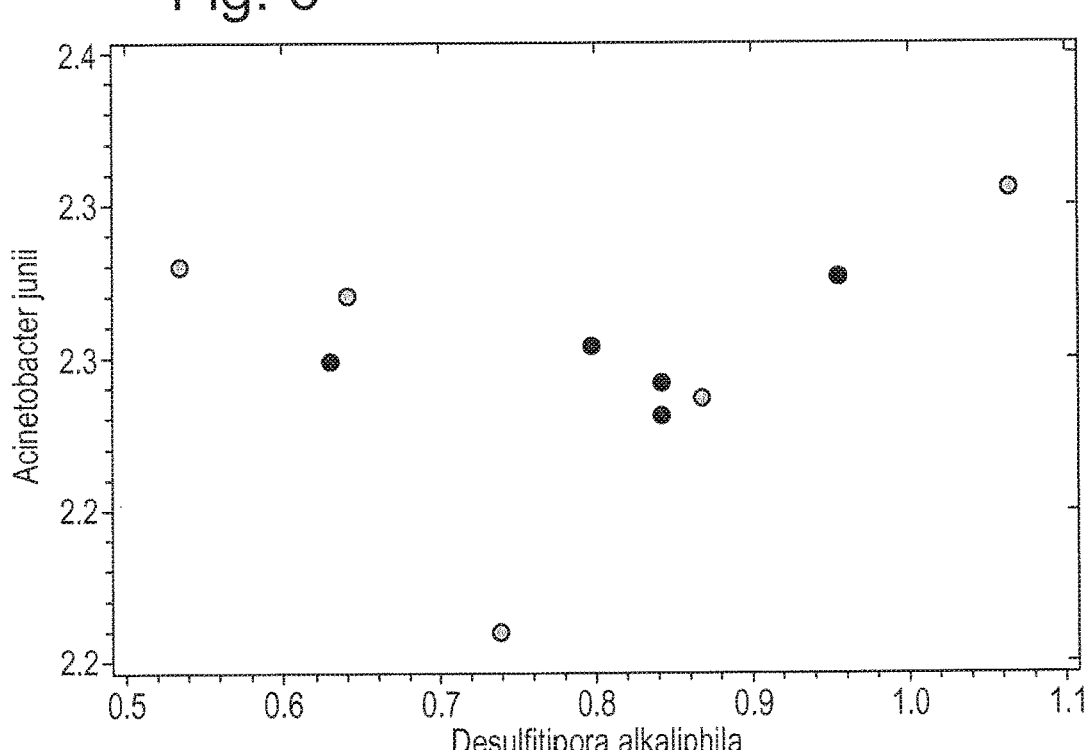
FIG. 6 shows a 2D classification plot using *Acinetobacter junii* and *Desulfitispora alkaliphil* results from Example 1 Study 1 (low FODMAP diet response in IBS subgroup Constipation). Light grey=responders, Dark grey-non-responders.
Figures 7, 8:
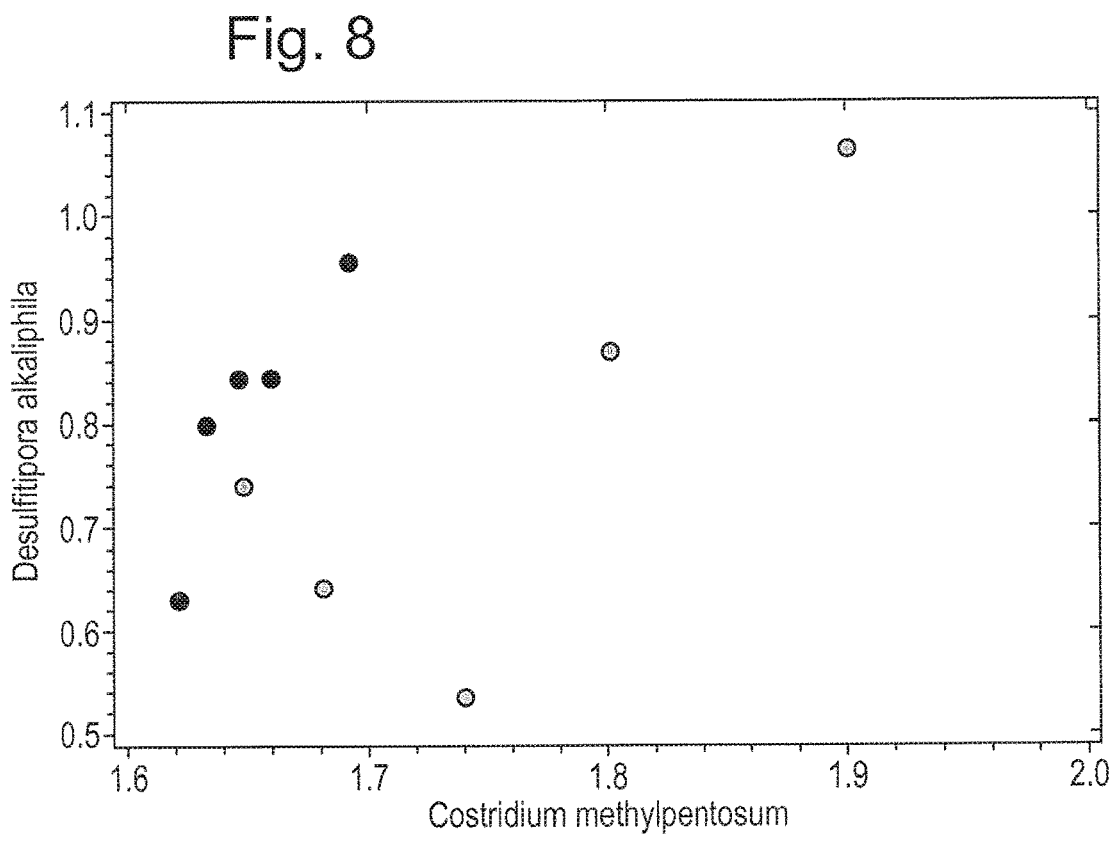
FIG. 7 shows a 2D classification plot using *Acinetobacter junii* and *Clostridium methylpentosum* results from Example 1 Study 1 (low FODMAP diet response in IBS subgroup Constipation). Light grey=responders, Dark grey-non-responders.
FIG. 8 shows a 2D classification plot using *Desulfitispora alkaliphila* and *Clostridium methylpentosum* results from Example 1 Study 1 (low FODMAP diet response in IBS subgroup Constipation). Light grey=responders, Dark grey-non-responders.
Figure 9:
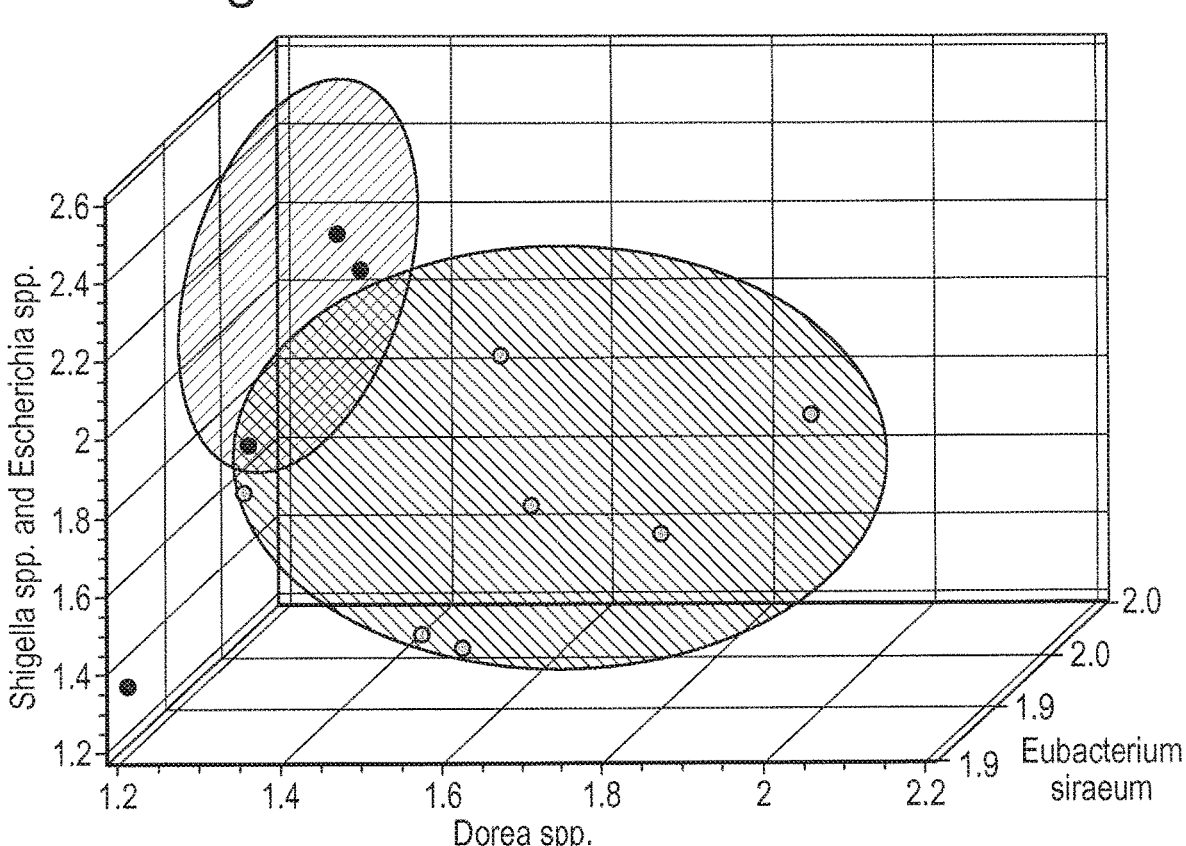
FIG. 9 shows a 3D classification plot using *Shigella* spp. and *Escherichia* spp., *Dorea* spp. and *Eubacterium siraeum* results from Example 1 Study 2 (low FODMAP diet response in IBS subgroup Diarrhoea). Light grey=responders, Dark grey-non-responders (accuracy 90.9%).
Figure 10:
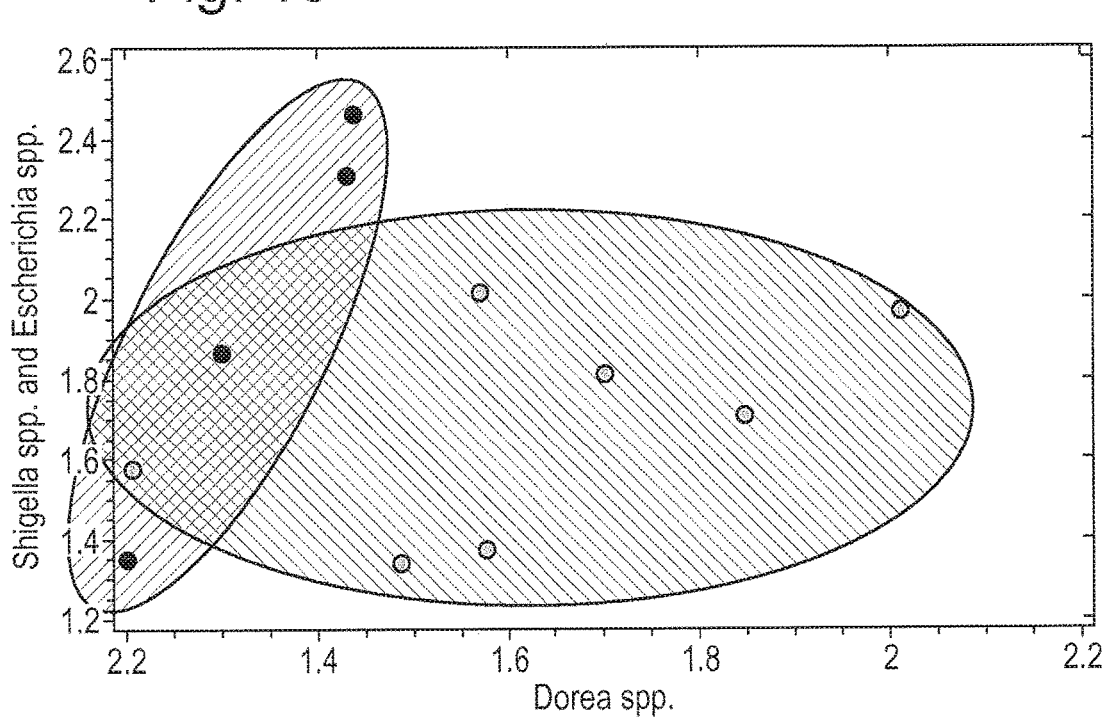
FIG. 10 shows a 2D classification plot using *Dorea* spp., and *Shigella* spp. and *Escherichia* spp. results from Example 1 Study 2 (low FODMAP diet response in IBS subgroup Diarrhoea). Light grey=responders, Dark grey=non-responders.
Figure 11:
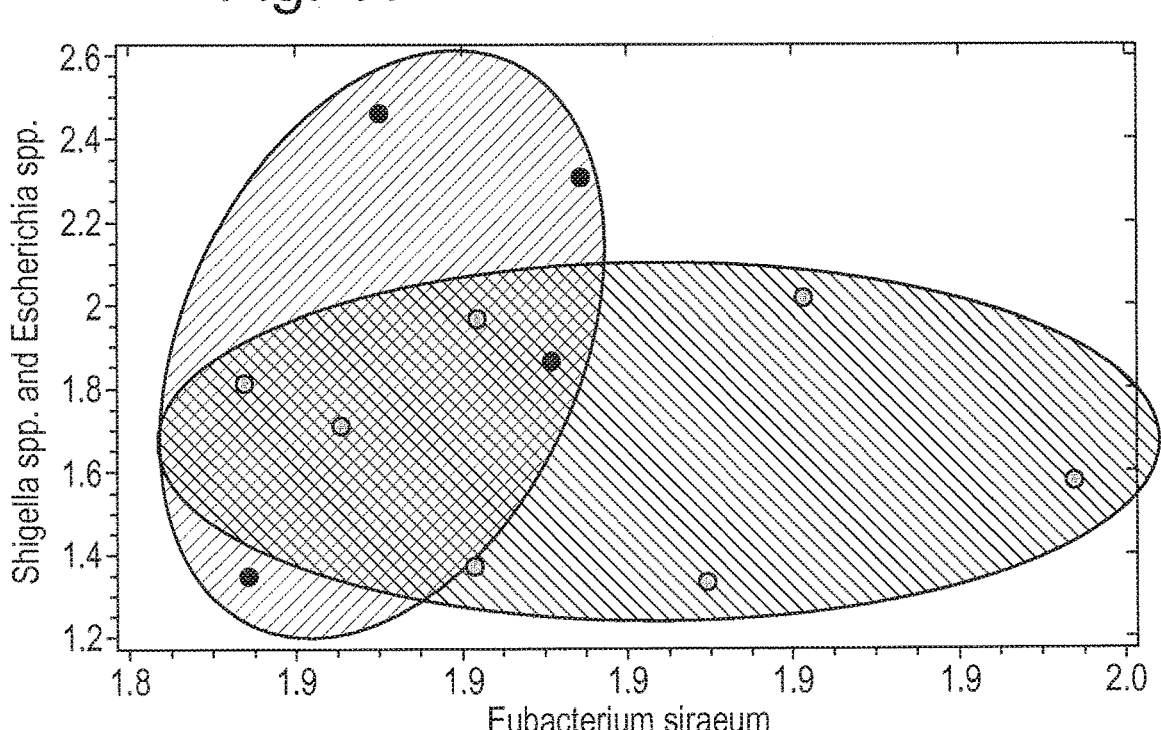
FIG. 11 shows a 2D classification plot using *Eubacterium siraeum*, and *Shigella* spp. and *Escherichia* spp. results from Example 1 Study 2 (low FODMAP diet response in IBS subgroup Diarrhoea). Light grey=responders, Dark grey=non-responders.
Figure 12:
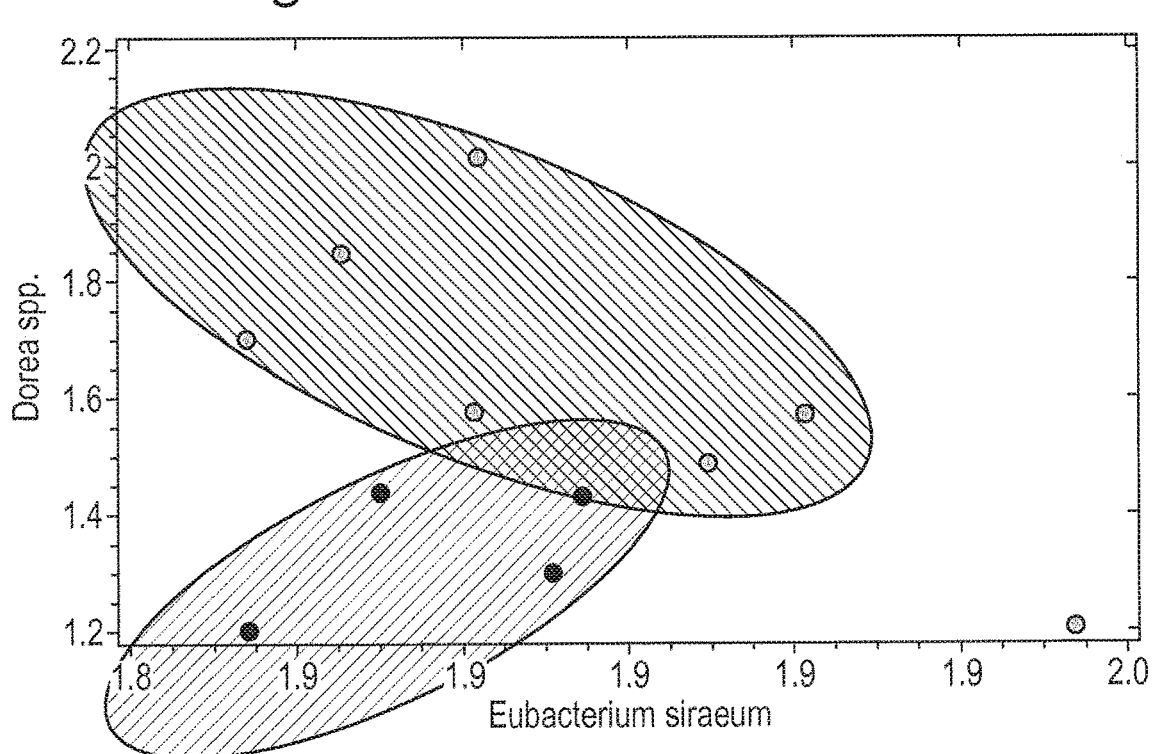
FIG. 12 shows a 2D classification plot using *Eubacterium siraeum* and *Dorea* spp. results from Example 1 Study 2
Figure 13:
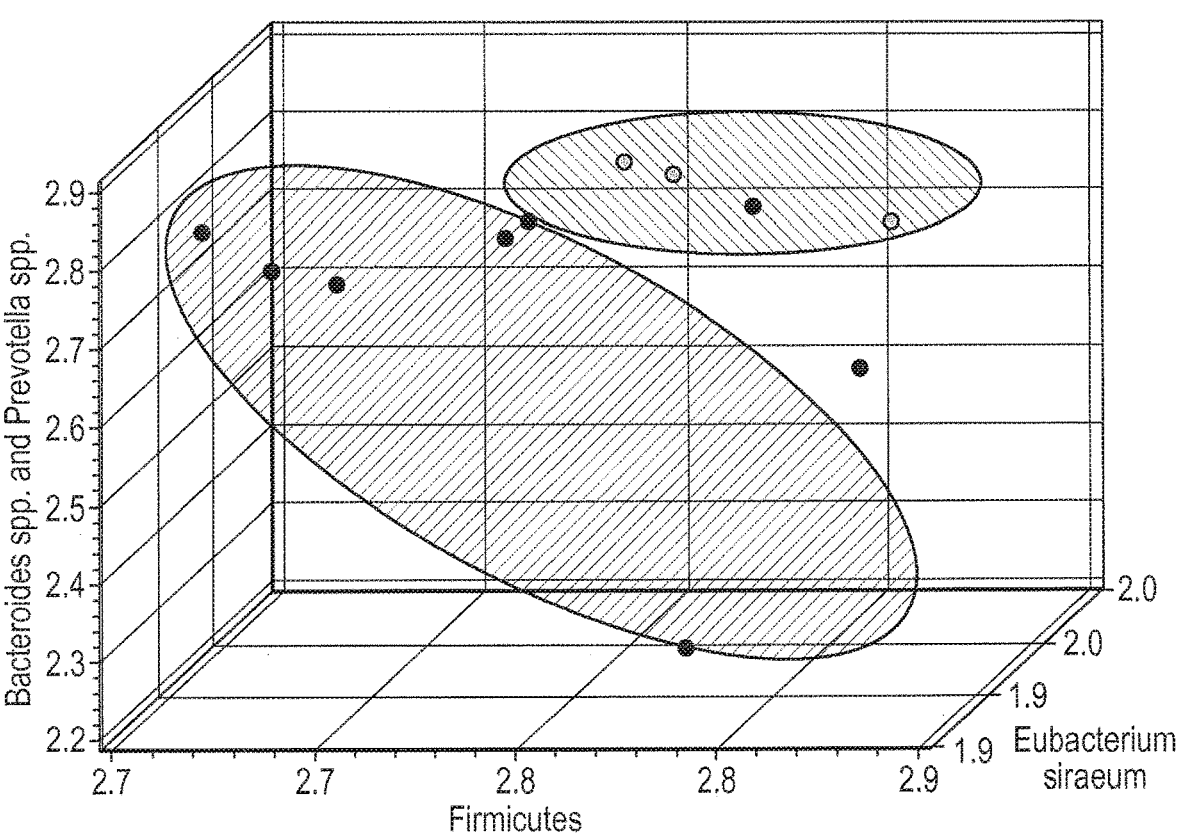

FIG. 13 shows a 3D classification plot using *Eubacterium siraeum*, Firmicutes and *Bacteroides* spp. and *Prevotella* spp. results from Example 1 Study 2 (high FOS diet response in IBS subgroup Diarrhoea). Light grey=responders, Dark grey=non-responders (accuracy 100%).

Figure 14:
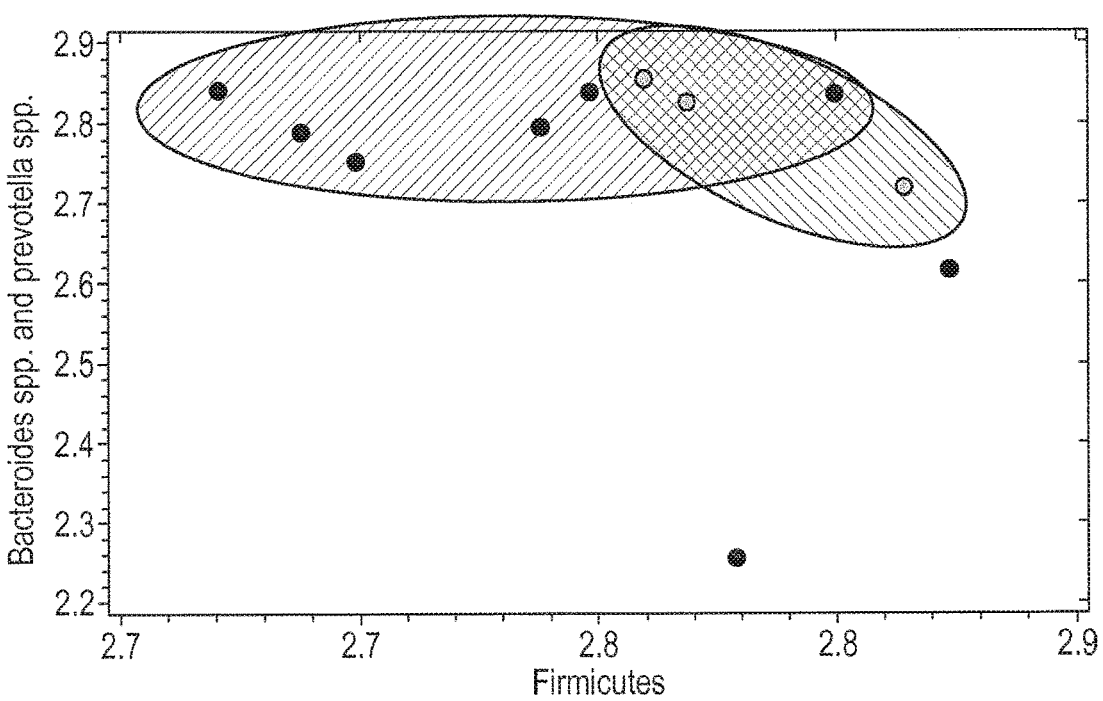

FIG. 14 shows a 2D classification plot using Firmicutes and *Bacteroides* spp. and *Prevotella* spp. results from Example 1 Study 2 (high FOS diet response in IBS subgroup Diarrhoea). Light grey=responders, Dark grey=non-responders.

Figure 15:
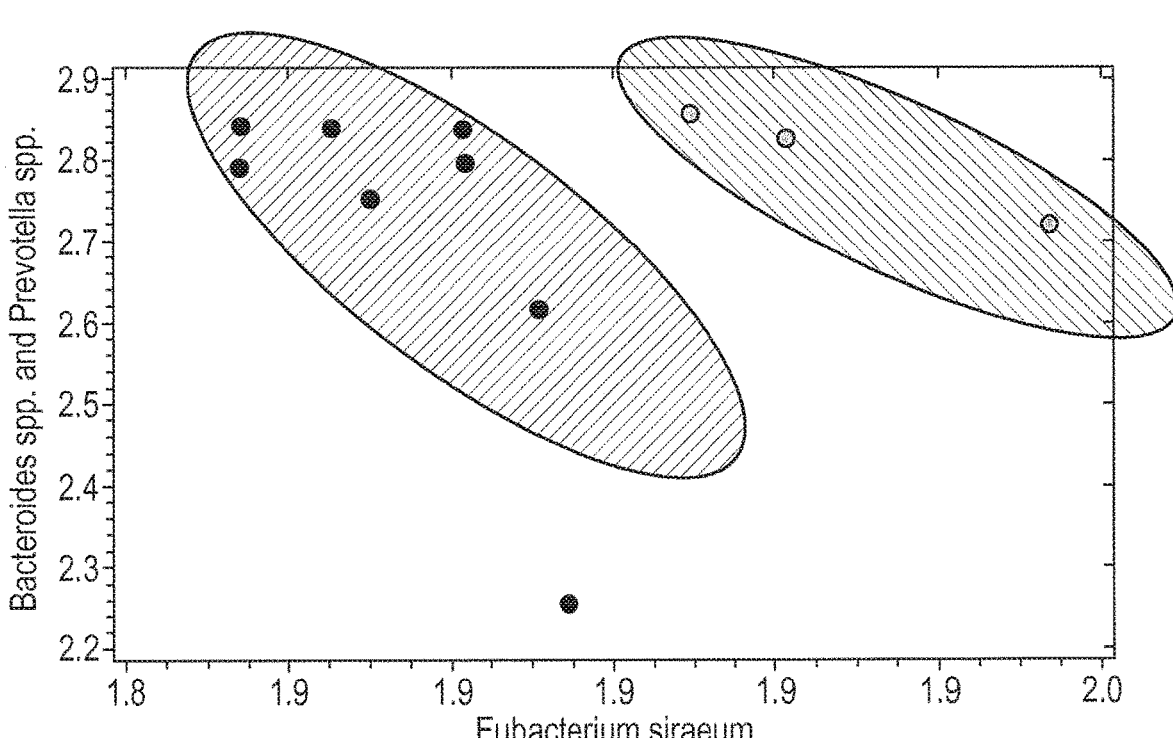

FIG. 15 shows a 2D classification plot using *Eubacterium siraeum* and *Bacteroides* spp. and *Prevotella* spp. results from Example 1 Study 2 (high FOS diet response in IBS subgroup Diarrhoea). Light grey=responders, Dark grey-non-responders.

Figure 16:
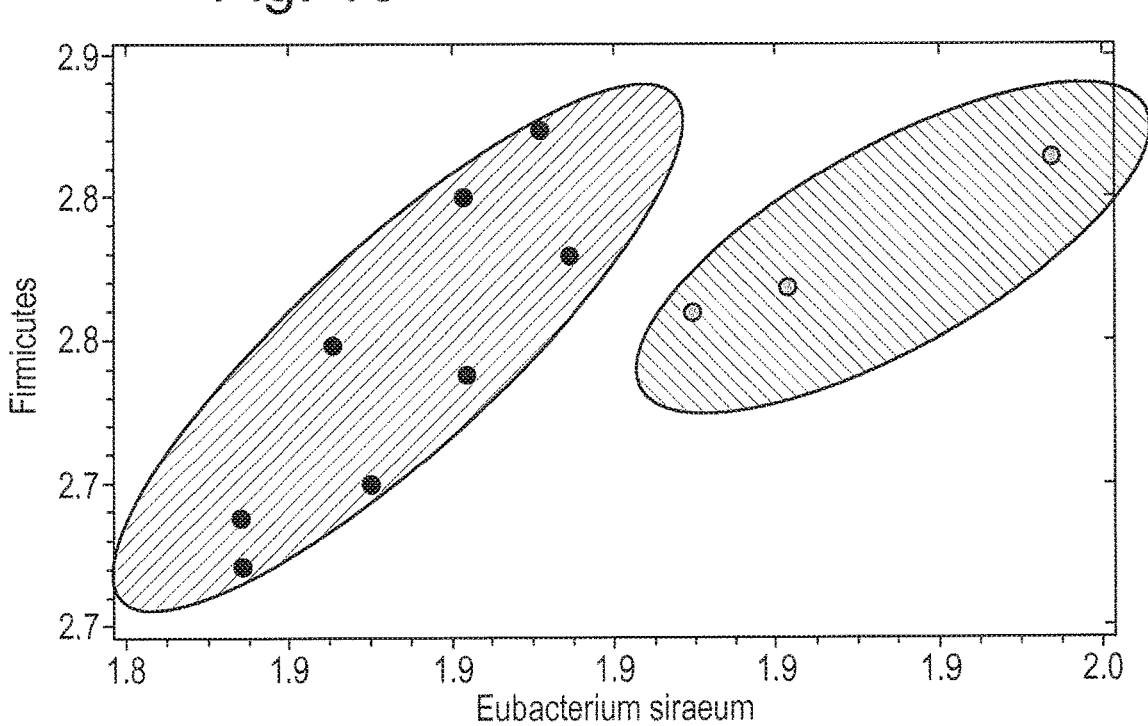
Figure 17:
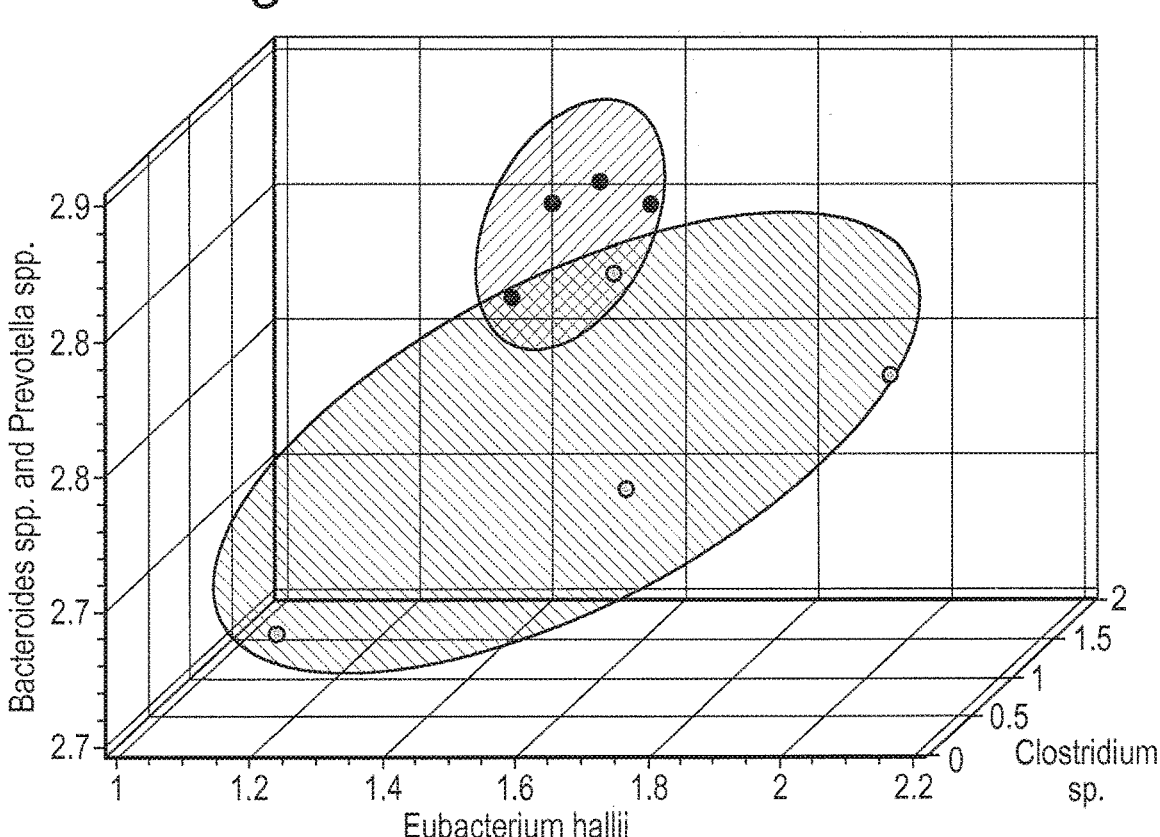

FIG. 16 shows a 2D classification plot using *Eubacterium siraeum* and Firmicutes results from Example 1 Study 2 (high FOS diet response in IBS subgroup Diarrhoea). Light grey=responders, Dark grey-non-responders. Subgroup diarrhoea FIG. 17 shows a 3D classification plot using *Bacteroides* spp. and *Prevotella* spp., *Eubacterium hallii*, and *Clostridium* sp. results from Example 1 Study 3 (FMT response in IBS subgroup Diarrhoea). Light grey=responders, Dark grey=non-responders (accuracy 100%).

Figure 18:
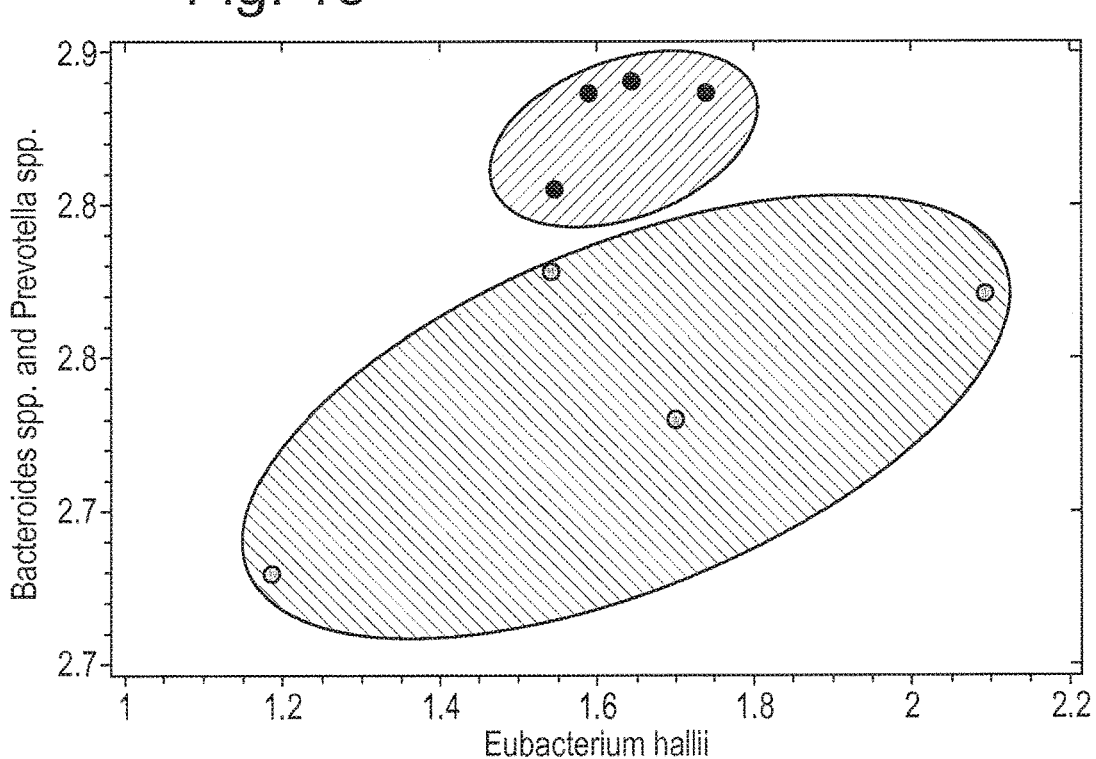

FIG. 18 shows a 2D classification-plot using *Bacteroides* spp. and *Prevotella* spp., and *Eubacterium hallii* results from Example 1 Study 3 (FMT response in IBS subgroup Diarrhoea). Light grey=responders, Dark grey=non-responders.

Figure 19:
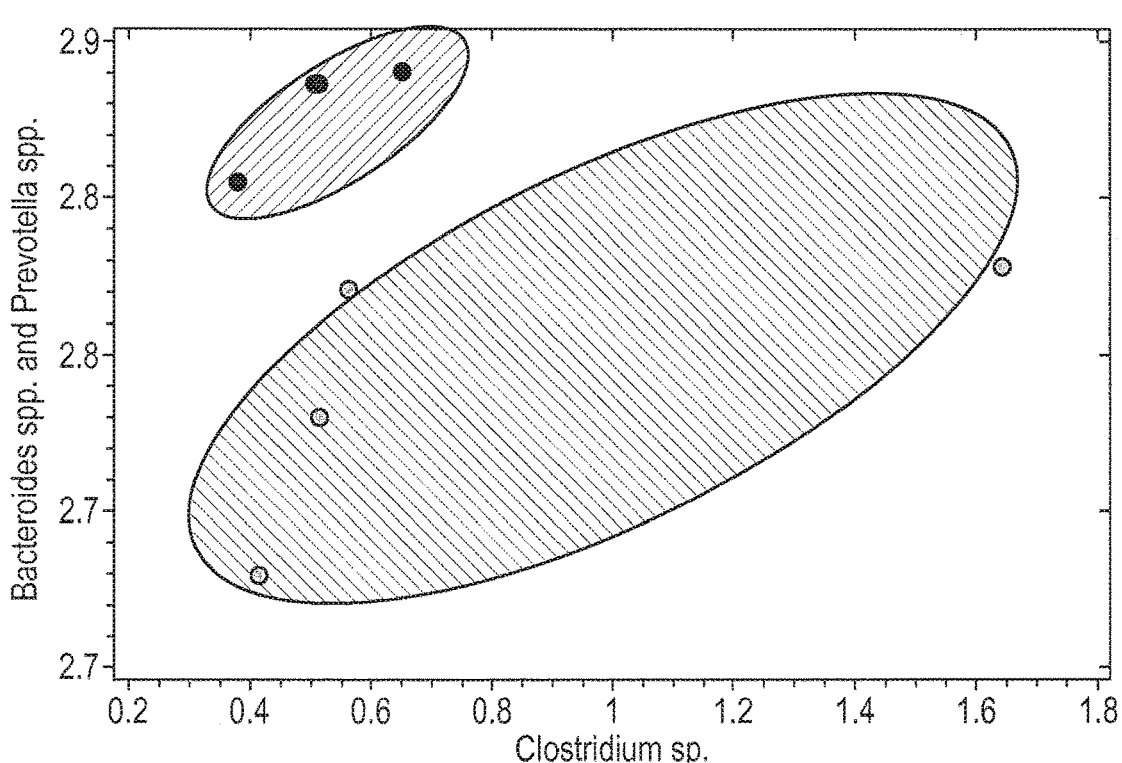

FIG. 19 shows a 2D classification plot using *Bacteroides* spp. and *Prevotella*, and *Clostridium* sp. results from Example 1 Study 3 (FMT response in IBS subgroup Diarrhoea). Light grey=responders, Dark grey=non-responders.

Figure 20:
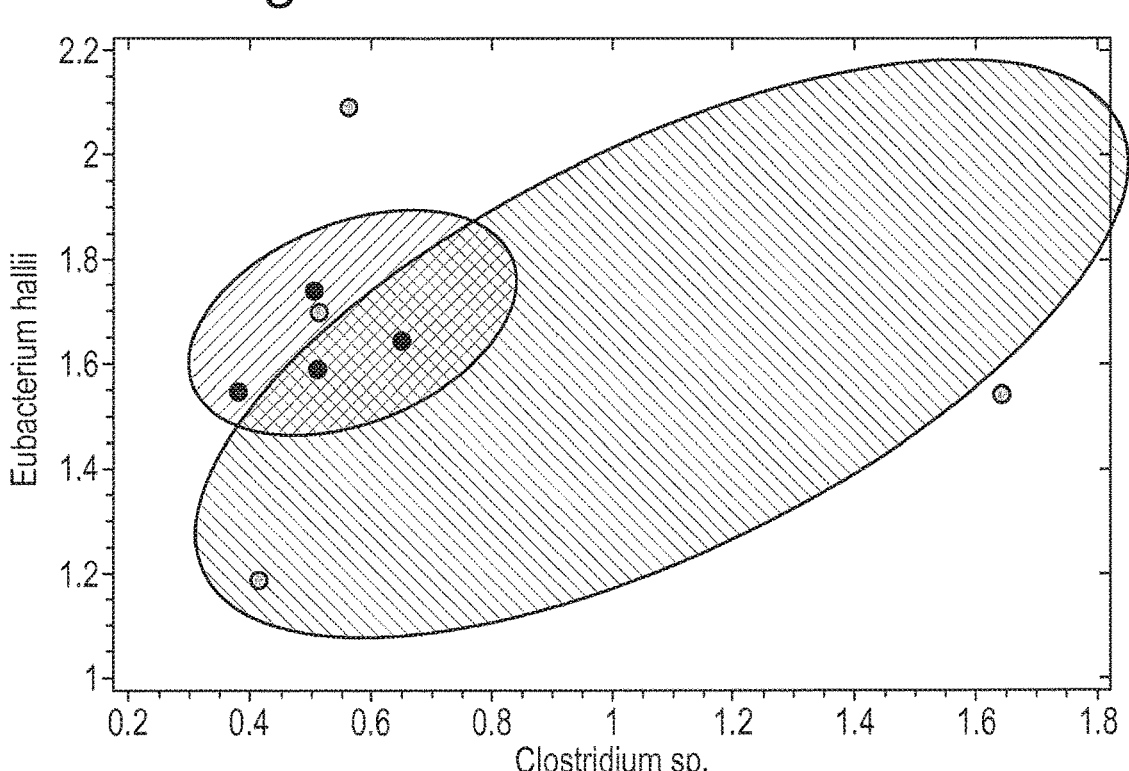

FIG. 20 shows a 2D classification plot using *Eubacterium hallii* and *Clostridium* sp. results from Example 1 Study 3 (FMT response in IBS subgroup Diarrhoea). Light grey=responders, Dark grey-non-responders.

Figure 21:
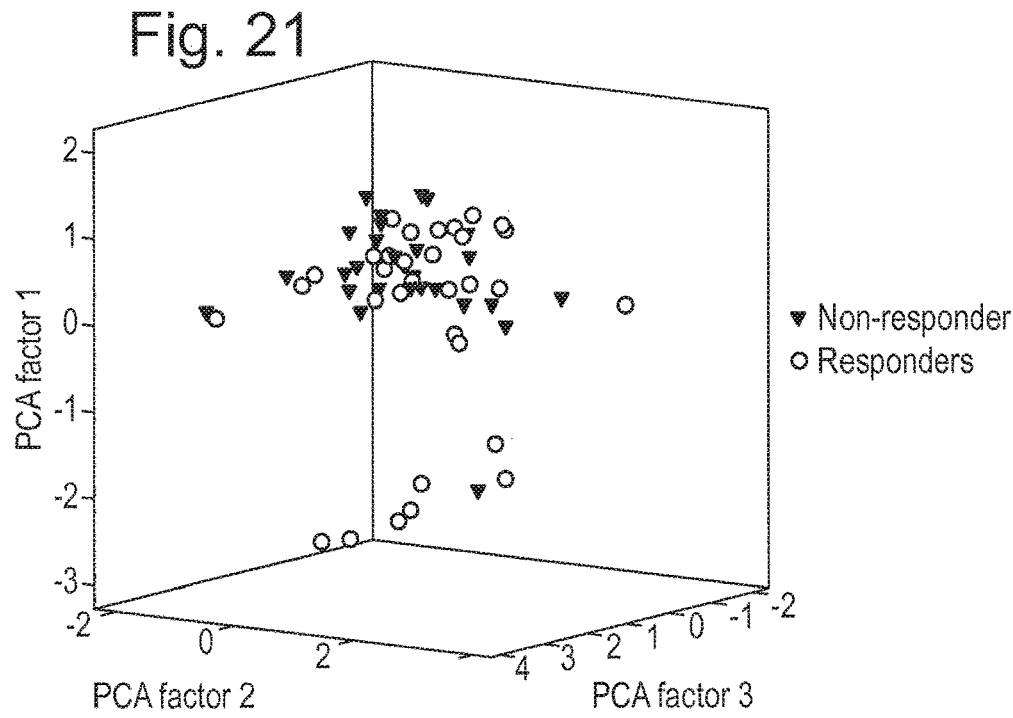

FIG. 21 shows a three-factor PCA of gut microbiota composition, as assessed by the GA-MAPR bacterial 16S rRNA gene Dysbiosis Test, in patients with IBS classified as responders (circles; n=32) and non-responders (triangles; n=29) to a 4-week FODMAP restricted diet, as described in Example 2.

Figure 22:
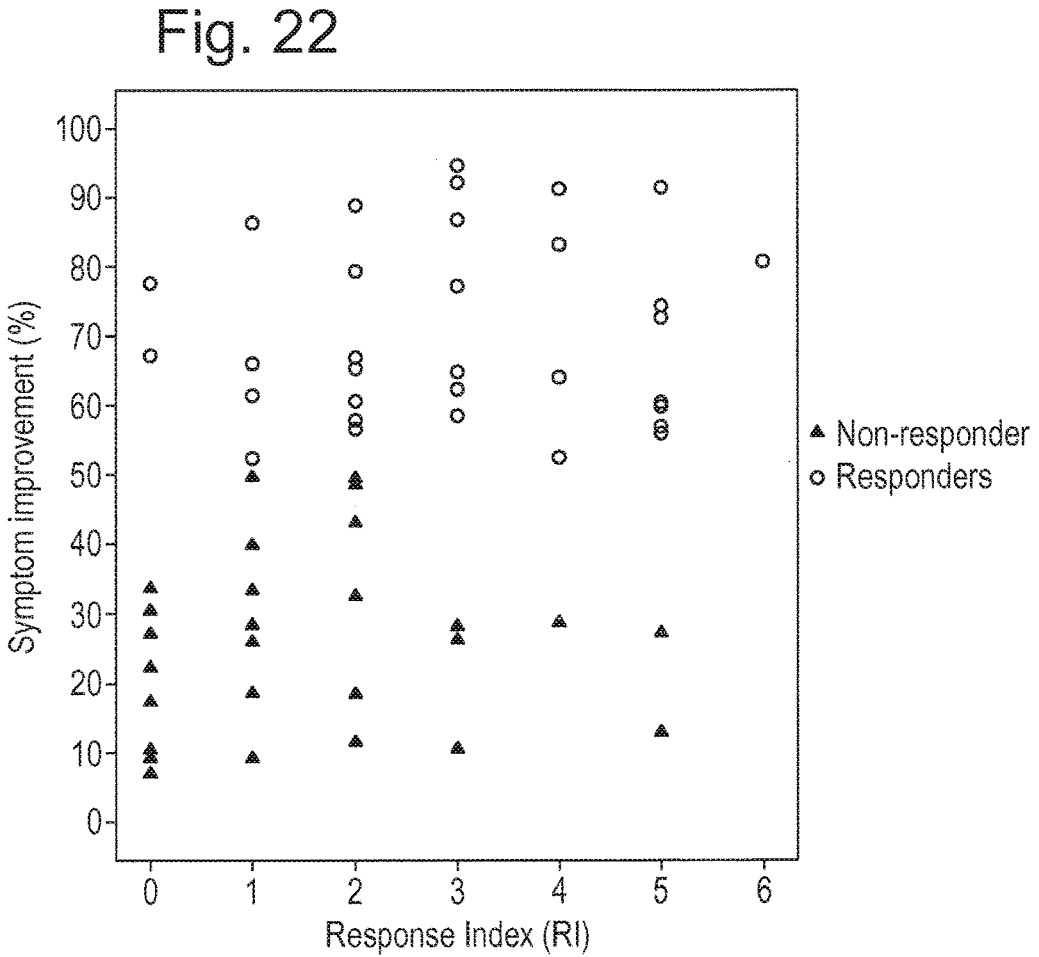

FIG. 22 shows the association between Response Index, based on gut microbiota composition results, and symptom response, as assessed as percentage reduction in IBS-SSS from baseline values, as described in Example 2 (responders (circles; n=32); non-responders (triangles; n=29)) The variables are significantly correlated (rho=0.39, p<0.001).

EXAMPLES

The invention will be further described with reference to the following non-limiting Examples.

Example 1—Identification of Bacterial Taxonomic Groups Capable of Discriminating IBS Patients Who Respond to a Low Fodmap Diet, A High Diet or FMT from Non-Responders Methods Clinical studies were performed to identify taxonomic groups from within GI tract microbiota which may serve as markers for IBS patients who respond to a low FODMAP diet (as defined in Gearry R. B et al, JCC 2008.09.004 8-14), a high FOS diet (as defined in Slavin J. Nutrients. 2013 April; 5(4): 1417-1435) FMT (as defined in Francis C. Y., Aliment Pharmacol Ther. 1997 April; 11(2): 395-402).

Patients were recruited in accordance with ROME III criteria for IBS diagnosing. Patients were IBS subtyped based on their predominant symptom into the following subtypes: Diarrhoea, Constipation or Mixed. Microbiota profiles from faecal samples from each patient were prepared using the GAmap™ Dysbiosis Test (Genetic Analysis AS, Oslo, Norway) before treatment and after 3-6 weeks in diet the diet intervention studies and after 1 and 3 weeks in the FMT studies. At these time patients provided an IBS-Symptom Severity Score (IBS-SSS; as defined in Francis C. Y., Aliment Pharmacol Ther. 1997 April; 11(2):395-402) is recorded, and this score is used to define responders/non-responders based on changes in score.

The GAmap™ test is based on conventional molecular biology techniques, comprising human faecal sample homogenisation and mechanical bacterial cell disruption; automated total bacterial gDNA extraction using magnetic beads; 16S rRNA PCR DNA amplification covering V3-V9; probe labelling by single nucleotide extension; hybridisation to complementary probes coupled to magnetic beads; and signal detection using BioCode 1000A 128-Plex Analyzer (Applied BioCode, Santa Fe Springs, CA, USA). The GAmap™ consists of 54 DNA probes which target≥300 bacteria on different taxonomic levels and which have been selected based on the ability to distinguish between IBS patients and healthy patients (i.e. patients non-symptomatic for IBS). The model algorithmically assesses the relative abundance of the target bacterial taxonomic groups within faecal samples and thereby provides a profile of the microbiota in the sample and can determine potential clinically relevant deviations in the microbiome from normobiosis, i.e. dysbiosis (Casén, C., et al, Alimentary Pharmacology and Therapeutics, 42(1):71-83).

A stepwise discriminant analysis was performed on the GAmap™ results, using the pre-intervention (baseline) bacteria probe values as candidate variables to characterise the responders and non-responders to the intervention (low FODMAP, high FOS, FMT). The procedure selected the bacteria candidates which best separated the responders from the non-responders. A responder was defined as having at least 50% reduction (diet interventions) or at least 100 point reduction (FMT) in total IBS score from baseline to post intervention. The selected variables were then used in a Fisher's linear discriminant function in order to quantify the impact of the selected variables and to estimate the accuracy, including sensitivity and specificity of the classification rule.

The coefficients in the discriminant function were chosen in order to maximize the difference in score of the discriminant function for the two groups (i.e. a positive discriminant score indicates a responder while a negative score indicates a non-responder patient). The interpretation of a 'high' value or a 'low' value for a bacteria in the Linear discriminant function is a relative measure between the groups. A high value for a bacteria will contribute to a classification that the patient as a responder, while a low value will do the reverse, when arranged so that a responder gives a positive function value.

Results

Study 1 (IBS01-1302)—IBS-Diarrhoea Patients on Restricted Fodmap Diet

Discriminant analysis at visit 1 for the subgroup Diarrhea (n=32, 16+16) on the responder/non-responder groups for the 54 bacteria probes (Responders classified as having at least 50% reduction in total IBS-score from baseline to week 4 of restricted FODMAP diet):

The following 6 bacteria probes were selected in a discriminant stepwise selection process * among the 54 candidates:

*Bacteroides* spp.
*Bacteroides stercosis*
*Bacteroides zoogleoformans*
*Acinetobacter junii*
Firmicutes
*Veillonella* spp., *Helicobacter* spp., and Clostridia
* A stepwise variable selection using a significance level of 0.10 as cutoff for inclusion and exclusion was applied The responders tended to have the following baseline characteristics:

Lower values of *Bacteroides* spp.
Higher values of *Bacteroides stercosis*
Higher values of *Bacteroides zoogleoformans*
Higher values of *Acinetobacter junii*
Lower values of Firmicutes
Lower values of *Veillonella* spp., *Helicobacter* spp., and Clostridia Out of 32 IBS-Diarrhoea patients, 31 (97%) were correctly classified based on the above: 16/16 responders (100%) and 31/32 non-responders (94%)

Study 1 (IBS01-1302)—IBS Constipation Patients on Restricted Fodmap Diet

Discriminant analysis at Visit 1 for the subgroup Constipation (n=10, 5+5) on the responder/non-responder groups for the 54 bacteria probes (Responders classified as having at least 50% reduction in total IBS-score from baseline to week 4 of restricted FODMAP diet):

The following 4 bacteria probes were selected in a discriminant stepwise selection process * among the 54 candidates:

*Eubacterium siraeum*
*Acinetobacter junii*
*Clostridium methylpentosum*
*Desulfitispora alkaliphila*
* A stepwise variable selection using a significance level of 0.10 as cutoff for inclusion and exclusion was applied The responders tended to have the following baseline characteristics:

Higher values of *Eubacterium siraeum*
Lower values of *Acinetobacter junii*
Higher values of *Clostridium methylpentosum*
Lower values of *Desulfitispora alkaliphila*
Out of 10 INS-Constipation patients, all 10 (100%) were correctly classified based on the above.

Study 2 (COP1602)—IBS Diarrhoea Patients on Restricted Fodmap Diet

Discriminant analysis using baseline bacteria for the subgroup IBS-Diarrhea on the responder/non-responder (n=11, 7/4) groups for the 54 bacteria probes. (Responders classified as having at least 50% reduction in total IBS-score from baseline to week 3 of the restricted FODMAP diet):

The following 3 bacteria probes were selected in a discriminant forward selection process * among the 54 candidates:

*Dorea* spp.
*Eubacterium siraeum*
*Shigella* spp. and *Escherichia* spp.
* A forward variable selection using a significance level of 0.10 as cutoff for inclusion was applied The responders tended to have the following baseline characteristics:

Higher values of *Dorea* spp.
Higher values of *Eubacterium siraeum*
Lower values of *Shigella* spp. and *Escherichia* spp.

Out of 11 IBS-Diarrhoea patients, 10 (90.9%) were correctly classified based on the above: 6/7 responders (85.7%) and 4/7 non-responders (100%)

Study 2 (COP1602)—IBS-Diarrhoea Patients on High Fos Diet

Discriminant analysis for high FOS diet responder/non-responder groups for the 54 bacteria probes (Responders classified as having at least 50% reduction in total IBS-score from baseline to week 6 of FOS diet)

The following 3 bacteria probes were selected in a discriminant stepwise selection process * among the 54 candidates:

*Eubacterium siraeum*
Firmicutes
*Bacteroides* spp. and *Prevotella* spp.
* A stepwise variable selection using a significance level of 0.10 as cutoff for inclusion and exclusion was applied The responders tended to have the following baseline characteristics:

Higher values of *Eubacterium siraeum*
Higher values of Firmicutes
Higher values of *Bacteroides* spp. and *Prevotella* spp.

Out of 11 IBS-Diarrhorea patients, all 11(100%) were correctly classified based on the above.

Study 3 (COP1609)—IBS-Diarrhoea Patients Treated with Faecal Microbiota Transplant Discriminant analysis using baseline bacteria for the subgroup IBS-Diarrhea on the responder/non-responder (n=8, 4/4) groups for the 54 bacteria probes (Responders classified as having at least 100 reduction in total IBS-score from baseline to week 3 after fecal transplant) (3 patients used WI as baseline):

The following 3 bacteria probes were selected in a discriminant forward selection process * among the 54 candidates:

*Clostridium* sp.
*Eubacterium hallii*
*Bacteroides/Prevotella*
* A forward variable selection using a significance level of 0.10 as cutoff for inclusion was applied The responders tended to have the following baseline characteristics:

Higher values of *Clostridium* sp.
Higher values of *Eubacterium hallii*
Lower values of *Bacteroides/Prevotella*

All of the 8 IBS-Diarrhea patients were correctly classified based on the above

Study 3 (COP1609)—IBS-Diarrhoea and IBS-Mix Patients Treated with Faecal Microbiota Transplant Discriminant analysis using baseline bacteria for the subgroup Diarrhea/Mix on the responder/non-responder (n=13, 5/8) groups for the 54 bacteria probes (Responders classified as having at least 100 reduction in total IBS-score from baseline to week 3 after fecal transplant) (3 patients used WI as baseline):

The responders tended to have the following baseline characteristics:

Higher values of *Clostridium* sp.
Lower values of *Dialister invisus*
Lower values of *Bacteroides/Prevotella*

All of the 13 Diarrhea/Mix patients were correctly classified based on the above.

Example 2—Exploring Gut Microbiota Composition as an Indicator Of Clinical Response to Dietary Fodmap Restriction in Patients With Irritable Bowel Syndrome

Materials and Methods

Patients

Patients with IBS were recruited consecutively from a secondary care outpatient clinic (Lovisenberg Diaconal Hospital, Oslo, Norway) between April 2013 and October 2014. In brief, all patients fulfilled the Rome III criteria for IBS, and were thoroughly examined by the same experienced gastroenterologist to exclude organic diseases. Of note, all patients underwent a $^{13}$C-D-xylose breath test to exclude small intestinal malabsorption, and only patients with high levels of $^{13}$CO_2 excretion following $^{13}$C-D-xylose ingestion were included.

Dietary Fodmap Restriction

All patients were referred to nutritional counselling by an experienced clinical dietician, educated within the low-FODMAP concept. Baseline diets were carefully evaluated to ensure that none of the patients had a particularly restricted diet compared to an average Norwegian diet before entering the study. Of note, the low-FODMAP diet was not well-known in Norway at the time of inclusion. The patients were then instructed to strictly eliminate all foods containing excessive amounts of FODMAPs, according to the principles given by the Monash University (Melbourne, Australia). Thus, the patients were instructed to avoid foods containing galacto-oligosaccharides (e.g., beans, lentils, peas, etc.), fructans (e.g., wheat, cabbage, onion, etc.), lactose (e.g., milk, yoghurt, dairy products, etc.) and polyols (e.g., mushrooms, cauliflower, apricots, etc.—including foods sweetened with polyols), as well as foods containing fructose in excess of glucose (e.g., apples, pears, dried fruits, etc.). Food items with low content of FODMAPs, such as oranges, bananas, rice, oats, meat, fish, eggs and lactose-free dairy products, were suggested as alternatives to food items with high content of FODMAPs. The duration of the dietary intervention was 4 weeks. Throughout the study, adherence to the diet was ensured by close follow-up by the clinical dietician, including personal consultations, telephone and e-mail correspondence, and dietary compliance was assessed by evaluation of food diaries that the patients were requested to fill in.

Evaluation of Symptoms and Definition of Response to Diet

Severity of abdominal symptoms was assessed before and after the dietary intervention by using the irritable bowel severity scoring system (IBS-SSS), according to Francis et al. (supra). The maximum achievable score of this inventory is 500 points, allowing grading of symptom severity as follows: mild (75-175 points), moderate (175-300 points) and severe (>300 points). As recommended by the Rome Design of Treatment Trials Committee, responders to dietary intervention were defined as patients reporting≥50% decrease on IBS-SSS. Accordingly, non-responders were defined as patients reporting<50% decrease on IBS-SSS.

In addition to abdominal symptom assessment, severity of extra-intestinal symptoms was evaluated at baseline, using the Hospital Anxiety and Depression Scale (HADS) for evaluation of anxiety and depression, and the Fatigue Impact Scale (FIS) for evaluation of chronic fatigue.

Analysis of Gut Microbiota Composition

Patients collected faecal samples before and after the dietary intervention by using designated containers (Genetic Analysis, Oslo, Norway). They were carefully instructed to freeze the samples immediately at minus 20° C. at home and bring the frozen containers to the hospital as soon as possible. The specimens were thereafter stored at minus 80° C. and not thawed until analysis. To assess gut microbial composition, we used the GA-MAPR bacterial 16S rRNA gene Dysbiosis Test (supra). Results are provided both as relative abundances of bacteria according to the 54 targeted bacterial markers, measured as "fluorescence signal strength", and as a Dysbiosis Index (DI; range 0-5), where DI>2 is denoted as "dysbiotic".

Statistical Methods

Due to a limited sample size, all continuous variables were compared between responders and non-responders by using non-parametric tests; Mann-Whitney Wilcoxon test when comparing unrelated variables, and Wilcoxon Signed Ranks test when measurements before and after treatment were compared. Possible associations between pairs of categorical variables were assessed using Chi-square test or McNemar test when comparing proportions before and after treatment. Correlation was computed using the Spearman's rho. To explore discrimination ability of all the measured bacterial markers to distinguish between responders and non-responders, we performed principal component analysis (PCA) using a covariance matrix. The probability of being a responder was calculated using logistic regression and the results were expressed as odds ratios (OR) with 95% confidence intervals (CI). In addition, probabilities given selected covariates were calculated. Positive predictive value (PPV) was calculated as described by Altman (Altman D G, et al, Statistics with confidence. 2nd ed. New York: BMJ Books; 2000). Due to a limited sample size, we were not able to divide our data into a training set and a test set, so model evaluation was performed using 5-fold cross-validation (CV) (James G, et al, An introduction to statistical learning. New York: Springer; 2013). The accuracy was computed as a mean score from CV with a 95% CI. Since our analyses were considered exploratory, no correction for multiple testing was performed and p-values<0.05 were considered statistically significant. All analyses were performed using SPSS version 22 and R (programming language), version 3.3.2.

Results

Subject Characteristics: Responders and Non-Responders 63 patients were initially enrolled; however, faecal samples for gut microbiota composition analysis from 2 patients were missing, reducing the total number of participants to 61. Based on the responder definition (≥50% decrease on IBS-SSS (13)), 32 patients were classified as responders and 29 patients as non-responders of the dietary intervention. Responders and non-responders did not differ significantly regarding clinical baseline characteristics (Table 1).

TABLE 1

COMPARISON OF BASELINE CHARACTERISTICS OF IBS PATIENTS CLASSIFIED AS RESPONDERS (N = 32) AND NON-RESPONDERS (N = 29) TO A 4-WEEK FODMAP RESTRICTED DIET

| Variable | Responders (n = 32) | Non-responders (n = 29) | P-value |
|---|---|---|---|
| Females, n (%) | 29 (91) | 25 (86) | 0.70 |
| Age, years, median (range) | 32.5 (19-67) | 39 (25-66) | 0.05 |
| BMI, kg/m², median (range) | 25.3 (17.7-35.8) | 23.4 (18.2-30.2) | 0.18 |
| IBS subtype, n (%) | | | 0.93 |
| IBS-D | 16 (50) | 16 (55) | |
| IBS-C | 5 (16) | 5 (17) | |
| IBS-M | 11 (34) | 8 (28) | |
| IBS-SSS, median (range) | | | |
| Total IBS-SSS score | 294 (174-449) | 281 (105-459) | 0.15 |
| Pain score | 107 (0-173) | 87 (0-196) | 0.07 |
| Bloating score | 64 (25-100) | 52 (0-97) | 0.19 |
| Bowel habit score | 72.5 (34-100) | 69 (34-100) | 0.49 |
| Life interference score | 69 (44-99) | 69 (35-99) | 0.42 |
| IBS severity, n (%) | | | 0.87 |
| Mild | 0 (0) | 0 (0) | |
| Moderate | 17 (53) | 16 (55) | |
| Severe | 15 (47) | 13 (45) | |
| HADS, median (range) | | | |
| Total HADS score | 14.5 (5-31) | 13 (0-31) | 0.55 |
| Anxiety score | 10 (2-18) | 8 (0-18) | 0.68 |
| Depression score | 4.5 (0-13) | 3 (0-13) | 0.23 |
| FIS, median (range) | 69.5 (12-155) | 75 (1-147) | 0.57 |

BMI = Body mass index;
IBS = Irritable bowel syndrome;
IBS-D = Diarrhoea-predominant IBS;
IBS-C = Constipation-predominant IBS;
IBS-M = IBS with mixed bowel habits;
IBS-SSS = irritable bowel syndrome severity scoring system;
HADS = Hospital Anxiety and Depression Scale;
FIS = Fatigue Impact Scale.

The gender distribution was similar in both groups, with a large majority being females. Body mass index (BMI) and distribution of IBS subtypes were also similar; however, responders tended to be slightly younger than non-responders.

There were no differences between responders and non-responders regarding any of the IBS-SSS measurements. The distribution of IBS-SSS categories was also very similar in both groups, and none of the patients were categorised as having mild IBS-SSS before treatment. However, after treatment 13 of the 32 responders reported mild IBS-SSS, while only one of the non-responders was in this category after treatment. Following treatment, both groups reported statistically significantly lower scores of IBS-SSS compared to baseline (both p<0.01).

Gut Microbiota Profiling

Bacterial profiles of responders and non-responders were compared based upon data from 54 bacterial markers. The overall ability of all measured bacterial markers to distinguish between responders and non-responders was assessed using the PCA method. The three-factor solution is depicted in FIG. 21. The responders had significantly higher levels for the following bacterial markers (Table 2): *Bacteroides fragilis, Acinetobacter junii*, Ruminiclostridium, *Streptococcus* and *Eubacterium* (all p<0.05). Furthermore, the responders had significantly lower levels for the following bacterial markers (Table 2): Clostridia/Negativicutes/Bacilli (Firmicutes), Actinomycetales, *Anaerotruncus*, Clostridiales and *Shigella* spp. and *Escherichia* spp. (all p<0.05).

TABLE 2

BACTERIAL ABUNDANCE IN BASELINE FAECAL SAMPLES
COLLECTED FROM RESPONDERS AND NON-RESPONDERS TO
A LOW FODMAP DIET. THE RESULTS ARE LISTED AS
MEDIAN INTENSITY SIGNAL WITH 25-75
PERCENTILES OF THE BACTERIAL DNA MARKERS.

| Microbial target | Responders (n = 31) | Non-responders (n = 29) | p-value[*] |
|---|---|---|---|
| *Bacteroides fragilis* [s] | 27.4 (11.1-58.6) | 8.0 (5.2-45.7) | 0.04 |
| *Acinetobacter junii* | 188.9 (178.9-195.7) | 177.4 (172.5-189.1) | 0.02 |
| *Ruminiclostridium* [g] | 51.3 (46.2-63.2) | 45.7 (42.9-50.7) | 0.01 |
| *Clostridia* [cl], *Negativicutes* [cl], *Bacilli* [cl] (*Firmicutes*) | 486.3 (385.6-597.0) | 622.5 (450.3-694.4) | 0.02 |
| *Streptococcus III* [g] | 13.8 (7.9-51.9) | 8.5 (5.8-11.9) | 0.03 |
| *Actinomycetales* [o] | 5.8 (1.2-9.6) | 10.0 (4.2-20.9) | 0.02 |
| *Anaerotruncus* [g] | 75.6 (63.7-90.4) | 83.7 (77.9-90.4) | <0.01 |
| *Clostridiales* [o] | 275.4 (248.4-300.0) | 285.5 (275.3-298.2) | <0.01 |
| *Eubacterium II* [g] | 32.5 (11.9-61.0) | 19.4 (10.7-61.4) | 0.03 |
| *Shigella* spp. [g], *Escherichia* spp. [g] | 12.2 (8.2-21.6) | 15.3 (10.7-22.9) | 0.04 | s = species;
g = genus;
o = order;
cl = class
[*]Mann-Whitney Wilkoxon test

For the remaining 44 bacterial markers, the data did not reveal any differences between responders and non-responders. The differences between responders and non-responders remained statistically significant also after treatment for 8 of the above described 10 bacterial markers. The two bacterial markers that were not statistically significant after diet were targeted at *Bacteroides fragilis* and *Acinetobacter junii*, as levels of these declined somewhat following treatment in the responder group (median 27.4 to 24.2, p=0.16 and median 188.9 to 183.6, p=0.19, for *Bacteroides fragilis* and *Acinetobacter junii*, respectively).

About half of the tested individuals were classified as "dysbiotic" (DI>2) before treatment, the proportions of responders and non-responders being were similar, 50% (16/32) and 48% (14/29), respectively. These proportions increased numerically but not statistically significantly after treatment and remained very similar for responders and non-responders; 56% (18/32) and 59% (17/29), respectively. However, many patients among both responders and non-responders changed their DI classification after treatment. For non-responders, 7 became "dysbiotic" and 5 "non-dysbiotic". The number of such patients was slightly smaller in the responders group, in which 5 became "dysbiotic" and 3 had a normal value of DI after treatment. When measured on a scale from 1-5, DI scores remained unchanged for both responders and non-responders after the treatment. The median (range) was 3 (1-4) for responders and 3 (1-5) for non-responders, both before and after treatment.

Response Index (R1)

Of the 54 bacterial markers used to assess gut microbial composition before treatment, 10 were significantly different between responders and non-responders (as described above). Based on median values of responders for these markers, a Response Index (RI) was constructed as follows:
1. The responders' median values for the 10 selected bacterial markers were used as cut-off levels.
2. Each patient was given a point when his/her value for each selected marker differed from the cut-off value. For each marker that was less abundant in responders than in non-responders, the patient was given a point when the level of said marker in his/her sample was lower than the cut-off level. For each marker that was more abundant in responders than in non-responders, the patient was given a point when the level of said marker was higher than the cut-off level.
3. The points were summed up, giving a number from 0 to 10 (RI sum score). This sum was further dichotomised: patients who scored 3 points and lower were assigned to value 0 (negative response) and patients who scored 4 or more points were assigned to value 1 (positive response).
4. Finally, the performance of RI was validated and accuracy computed as the mean score: 0.72, 95% CI [0.63:0.81].

Although there was a high diversity in our results before treatment, responders reached higher RI sum scores compared to non-responders (median 4.9 for responders and 2.6 for non-responders, range 0-9 for both). Further, there was a statistically significant correlation between the RI sum score and percentage decrease on IBS-SSS (rho=0.39, p<0.001; FIG. 22). A majority of responders reached high RI sum scores also after their treatment.

RI Before Treatment

In total, 60% (19/32) of the responders scored 4 points or higher on the RI sum score, whereas only 21% (6/29) of the non-responders had a positive RI. Responders were younger and had a slightly higher BMI, and further analyses were thus adjusted for these possible confounders. When adjusted for age and BMI, only being a responder remained strongly statistically associated with positive RI (p<0.004). However, age was kept in the final model. Patients with a positive RI were 5 times more likely to be responders compared to those who scored lower (OR=5.05, 95% CI [1.58:16.10]). Younger patients were more likely to be responders (p=0.04). The probability to respond for patients having a positive RI was 83.4%, 95% CI [61.2-94%]. Furthermore, we calculated the probability that a patient will respond to FODMAP diet given a positive RI, i.e. the positive predictive value: PPV=76.0, 95% CI [61.1-86.9].

RI after Treatment

A majority of responders had a positive RI also after treatment. In total, 56% (18/32) of the responders scored positively compared to 14% (4/29) of the non-responders. When adjusted for age and BMI, responders were more than 7 times more likely to score positive using the RI compared to non-responders (OR=7.31, 95% CI [1.90-28.23], p=0.004).

Discussion

During the last decade, increasing evidence that the gut microbiota plays an important role in IBS pathogenesis has emerged. Whereas mucosa-associated microbiota mainly seems to influence the host via regulatory control system located within the gut wall, luminal microbiota mainly seems to exert effects through fermentation, yielding gas and other metabolites. Both compartments seem to be disturbed in patients with IBS, and such alterations may be involved in symptom generation. In the present study, we evaluated the faecal microbiota composition by assessing bacterial DNA markers.

The present data suggest that pre-treatment levels of selected gut microbial DNA markers may be associated with higher probability to respond favorably to dietary FODMAP restriction. Although a mechanistic relationship between gut microbiota composition and IBS symptom generation cannot be ascertained from the present study, the results suggest that such microbial DNA markers may be used prior to treatment as an indicator of likely treatment response and thus may be of significant value in a clinical setting. The incorporation of information from such markers into a scoring system, e.g. the RI described herein, may allow for the straightforward, uniform and repeatable application of this assessment across clinical settings.

The invention claimed is:

1. An in vitro method to determine the likelihood that a subject with irritable bowel syndrome (IBS) will respond to treatment with a low Fermentable Oligosaccharides, Disaccharides, Monosaccharides and Polyols (FODMAP) diet, said method comprising (i) determining for a test sample from the gastrointestinal (GI) tract of a subject with constipation subtype IBS to be treated with a low FODMAP diet the amount of bacteria from at least one taxonomic group selected from Clostridium methylpentosum,
Eubacterium siraeum,
Acinetobacter junii, and
Desulfitispora alkaliphila; and (ii)(a) comparing the amount of said bacteria from said at least one taxonomic group with a reference value prepared from at least one sample from the GI tract of at least one subject non-symptomatic for IBS, and determining if the amount of said bacteria from said at least one taxonomic group in said test sample differs from, or corresponds to, the reference value, wherein an amount of bacteria in the taxonomic groups Clostridium methylpentosum or Eubacterium siraeum which is greater than the reference values, or an amount of bacteria in the taxonomic groups Acinetobacter junii or Desulfitispora alkaliphila which is lower than the reference values is indicative that the subject will respond to a low FODMAP diet; and/or (ii)(b) comparing the amount of said bacteria from said at least one taxonomic group with a cut-off value which has been determined as a median amount of said bacteria in at least one sample from the GI tract of at least one IBS subject with said IBS subtype which has been previously shown to be responsive to said treatment and determining if the amount of said bacteria from said at least one taxonomic group in said test sample is greater than or less than said median cut-off value, wherein an amount of bacteria in the taxonomic groups Clostridium methylpentosum or Eubacterium siraeum which is greater than said median cut-off value for said bacteria, or an amount of bacteria in the taxonomic groups Acinetobacter junii or Desulfitispora alkaliphila which ich is less than said median cut-off value for said bacteria is indicative the bis WI respond to a low FODMAP diet.

2. The method of claim 1, wherein the amounts of bacteria in at least 2 of said taxonomic groups are determined and in step (ii)(a) comparison is made with reference values for said taxonomic groups prepared from at least one GI tract sample from at least one subject non-symptomatic for IBS, and/or in step (ii)(b) comparison is made with cut-off values for said taxonomic groups prepared from at least one sample from the GI tract of at least one IBS subject with said IBS subtype and which has been previously shown to be responsive to said treatment.

3. The method of claim 1, wherein the method further comprises additionally determining the amount of bacteria in at least one taxonomic groups selected from Acinetobacter junii, Firmicutes, Shigella spp. and Escherichia spp., Bacteroides fragilis, Ruminiclostridium, Streptococcus, Actinomycetales, Anaerotruncus, Clostridiales, and Eubacterium, comparing said amount with a reference value for a sample from the GI tract of normobiotic subjects and/or a median cut off value for a sample from the GI tract of IBS subjects with constipation subtype IBS previously shown to be responsive to treatment with a low FODMAP diet and determining if the amount of said bacteria from said at least one taxonomic group in said test sample differs from, or corresponds to, the normobiotic reference value and/or is greater than or less than said median cut-off value.

4. The method of claim 1, wherein the amount of bacteria from the at least one taxonomic group is determined by a method of nucleic acid analysis.

5. The method of claim 1, wherein the sample from the GI tract is selected from (a) luminal contents of the GI tract,
(b) parts of the mucosa, the submucosa, the muscularis externa, the adventitia and/or the serosa of a GI tract tissue/organ,
(c) nucleic acid prepared from (a) or (b), or
(d) a microbial culture of (a) or (b).

6. The method of claim 1, wherein said GI tract sample is obtained from the jejunum, the ileum, the cecum, the colon, the rectum or the anus.

7. The method of claim 4, wherein the method of nucleic acid analysis is nucleic acid sequencing, oligonucleotide probe hybridisation, primer based nucleic acid amplification; antibody or other specific affinity ligand based detection; proteomic analysis or metabolomic analysis.

8. The method of claim 5, wherein the sample from the GI tract is luminal contents of the GI tract and wherein the luminal contents of the GI tract are stomach contents, intestinal contents, mucus and faeces/stool, or combinations thereof.

9. The method of claim 5, wherein the sample from the GI tract is nucleic acid prepared from (a) or (b) and the nucleic acid is prepared by reverse transcription and/or nucleic acid amplification.

* * * * *